US008652040B2

(12) United States Patent
LeBoeuf et al.

(10) Patent No.: US 8,652,040 B2
(45) Date of Patent: Feb. 18, 2014

(54) TELEMETRIC APPARATUS FOR HEALTH AND ENVIRONMENTAL MONITORING

(75) Inventors: Steven Francis LeBoeuf, Raleigh, NC (US); Jesse Berkley Tucker, Schenectady, NY (US); Michael Edward Aumer, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 1198 days.

(21) Appl. No.: 11/811,844

(22) Filed: Jun. 12, 2007

(65) Prior Publication Data

US 2008/0146890 A1    Jun. 19, 2008

Related U.S. Application Data

(60) Provisional application No. 60/905,761, filed on Mar. 8, 2007, provisional application No. 60/876,128, filed on Dec. 21, 2006, provisional application No. 60/875,606, filed on Dec. 19, 2006.

(51) Int. Cl.
*A61B 5/00* (2006.01)

(52) U.S. Cl.
USPC .......................................................... 600/301

(58) Field of Classification Search
USPC .................. 600/300–301; 381/71.1–71.14
See application file for complete search history.

(56) References Cited

U.S. PATENT DOCUMENTS

| | | | |
|---|---|---|---|
| 4,240,882 A | 12/1980 | Ang et al. | |
| 4,438,772 A | 3/1984 | Slavin | |
| 4,521,499 A | 6/1985 | Switzer | |
| 4,541,905 A | 9/1985 | Kuwana et al. | |
| 4,592,807 A | 6/1986 | Switzer | |
| 4,655,225 A | 4/1987 | Dahne et al. | |
| 5,022,970 A | 6/1991 | Cook et al. | |
| 5,079,421 A * | 1/1992 | Knudson et al. ............... | 250/343 |
| 5,348,002 A | 9/1994 | Caro | |
| 5,492,129 A | 2/1996 | Greenberger | |
| 5,499,301 A * | 3/1996 | Sudo et al. .................... | 381/71.3 |
| 5,711,308 A | 1/1998 | Singer | |
| 5,743,260 A | 4/1998 | Chung et al. | |
| 5,779,631 A | 7/1998 | Chance | |
| 5,853,005 A * | 12/1998 | Scanlon ........................ | 600/459 |
| 6,004,274 A | 12/1999 | Nolan et al. | |
| 6,045,511 A | 4/2000 | Ott et al. | |
| 6,283,915 B1 | 9/2001 | Aceti et al. | |
| 6,285,816 B1 | 9/2001 | Anderson et al. | |

(Continued)

FOREIGN PATENT DOCUMENTS

WO    WO 2013/038296 A1    3/2013

OTHER PUBLICATIONS

International Search Report and Written Opinion of the International Searching Authority, corresponding to PCT/US2007/025114, mailed May 13, 2008.

(Continued)

*Primary Examiner* — Bill Thomson
*Assistant Examiner* — Bobby Soriano
(74) *Attorney, Agent, or Firm* — Myers Bigel Sibley & Sajovec, P.A.

(57) ABSTRACT

Wearable apparatus for monitoring various physiological and environmental factors are provided. Real-time, noninvasive health and environmental monitors include a plurality of compact sensors integrated within small, low-profile devices, such as earpiece modules. Physiological and environmental data is collected and wirelessly transmitted into a wireless network, where the data is stored and/or processed.

57 Claims, 11 Drawing Sheets

(56) References Cited

U.S. PATENT DOCUMENTS

| | | | |
|---|---|---|---|
| 6,289,230 B1 | 9/2001 | Chaiken et al. | |
| 6,332,868 B1 | 12/2001 | Sato et al. | |
| 6,361,660 B1 | 3/2002 | Goldstein | |
| 6,443,890 B1 | 9/2002 | Schulze et al. | |
| 6,444,474 B1 | 9/2002 | Thomas et al. | |
| 6,454,718 B1 | 9/2002 | Clift | |
| 6,458,080 B1* | 10/2002 | Brown et al. | 600/300 |
| 6,470,893 B1 | 10/2002 | Boesen | |
| 6,514,278 B1 | 2/2003 | Hibst et al. | |
| 6,527,711 B1 | 3/2003 | Stivoric et al. | |
| 6,534,012 B1 | 3/2003 | Hazen et al. | |
| 6,556,852 B1 | 4/2003 | Schulze et al. | |
| 6,571,117 B1 | 5/2003 | Marbach | |
| 6,605,038 B1 | 8/2003 | Teller et al. | |
| 6,631,196 B1 | 10/2003 | Taenzer et al. | |
| 6,694,180 B1 | 2/2004 | Boesen | |
| 6,760,610 B2 | 7/2004 | Tschupp et al. | |
| 6,893,396 B2 | 5/2005 | Schulze et al. | |
| 6,953,435 B2 | 10/2005 | Kondo et al. | |
| 7,041,062 B2 | 5/2006 | Friedrichs et al. | |
| 7,043,287 B1 | 5/2006 | Khalil et al. | |
| 7,054,674 B2 | 5/2006 | Cane et al. | |
| 7,088,234 B2 | 8/2006 | Naito et al. | |
| 7,107,088 B2 | 9/2006 | Aceti | |
| 8,416,959 B2* | 4/2013 | Lott et al. | 381/71.6 |
| 2002/0143242 A1* | 10/2002 | Nemirovski | 600/300 |
| 2003/0007631 A1 | 1/2003 | Bolognesi et al. | |
| 2003/0064712 A1 | 4/2003 | Gaston et al. | |
| 2003/0220584 A1* | 11/2003 | Honeyager et al. | 600/559 |
| 2004/0004547 A1* | 1/2004 | Appelt et al. | 340/573.1 |
| 2004/0022700 A1 | 2/2004 | Kim et al. | |
| 2004/0120844 A1 | 6/2004 | Tribelsky et al. | |
| 2004/0138578 A1 | 7/2004 | Pineda et al. | |
| 2004/0186390 A1 | 9/2004 | Ross et al. | |
| 2004/0219056 A1 | 11/2004 | Tribelsky et al. | |
| 2004/0228494 A1* | 11/2004 | Smith | 381/67 |
| 2004/0242976 A1 | 12/2004 | Abreu | |
| 2005/0004458 A1* | 1/2005 | Kanayama et al. | 600/437 |
| 2005/0043630 A1* | 2/2005 | Buchert | 600/473 |
| 2005/0119833 A1 | 6/2005 | Nanikashvili | |
| 2005/0148883 A1 | 7/2005 | Boesen | |
| 2005/0177034 A1* | 8/2005 | Beaumont | 600/323 |
| 2005/0192515 A1* | 9/2005 | Givens et al. | 600/559 |
| 2005/0203349 A1 | 9/2005 | Nanikashvili | |
| 2005/0222487 A1* | 10/2005 | Miller et al. | 600/25 |
| 2005/0228244 A1* | 10/2005 | Banet | 600/301 |
| 2005/0258816 A1 | 11/2005 | Zen et al. | |
| 2005/0259811 A1* | 11/2005 | Kimm et al. | 379/430 |
| 2006/0064037 A1 | 3/2006 | Shalon et al. | |
| 2006/0084878 A1 | 4/2006 | Banet et al. | |
| 2006/0123885 A1 | 6/2006 | Yates et al. | |
| 2006/0205083 A1 | 9/2006 | Zhao | |
| 2006/0210058 A1 | 9/2006 | Kock et al. | |
| 2006/0240558 A1 | 10/2006 | Zhao | |
| 2006/0246342 A1 | 11/2006 | MacPhee | |
| 2007/0015992 A1* | 1/2007 | Filkins et al. | 600/407 |
| 2007/0027367 A1* | 2/2007 | Oliver et al. | 600/300 |
| 2007/0060800 A1* | 3/2007 | Drinan et al. | 600/300 |
| 2007/0063850 A1* | 3/2007 | Devaul et al. | 340/573.1 |
| 2007/0116314 A1* | 5/2007 | Grilliot et al. | 381/367 |
| 2008/0076972 A1* | 3/2008 | Dorogusker et al. | 600/300 |
| 2008/0114220 A1* | 5/2008 | Banet et al. | 600/301 |
| 2009/0030350 A1 | 1/2009 | Yang et al. | |
| 2009/0069645 A1* | 3/2009 | Nielsen et al. | 600/301 |
| 2009/0131761 A1* | 5/2009 | Moroney, III et al. | 600/301 |

OTHER PUBLICATIONS

Anpo et al. "Photocatalytic Reduction of $Co_2$ With $H_2O$ on Titanium Oxides Anchored within Micropores of Zeolites: Effects of the Structure of the Active Sites and the Addition of Pt" *J. Phys. Chem. B*, 101:2632-2636 (1997).

Bârsan et al. "Understanding the fundamental principles of metal oxide based gas sensors; the example of CO sensing with $SnO_2$ sensors in the presense of humidity" *Journal of Physics: Condensed Matter* 15:R813-R839 (2003).

Bott "Electrochemistry of Semiconductors" *Current Separations* 17(3):87-91 (1998).

Martins et al. "Zinc oxide as an ozone sensor" *Journal of Applied Physics* 96(3):1398-1408 (2004).

Saladin et al. "Photosynthesis of $CH_4$ at a $TiO_2$ Surface from Gaseous $H_2O$ and $CO_2$" *J. Chem. Soc., Chem. Commun.* 533-534 (1995).

Skubal et al. "Detection and identification of gaseous organics using a $TiO_2$ sensor" *Journal of Photochemistry and Photobiology A: Chemistry* 148:103-108 (2002).

Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 5-8, 2000, sponsored by SPIE, 10 pp.

Zhang et al. "Development of Chemical Oxygen Demand On-Line Monitoring System Based on a Photoelectrochemical Degradation Principle" *Environ. Sci. Technol.*, 40(7):2363-2368 (2006).

Fitrainer, http://itami.com.

European Search Report corresponding to European Application No. 07862660.3 dated Apr. 25, 2012; 7 pages.

* cited by examiner

TELEMETRIC APPARATUS FOR HEALTH AND ENVIRONMENTAL MONITORING

RELATED APPLICATION

This application claims the benefit of and priority to U.S. Provisional Patent Application No. 60/905,761, filed Mar. 8, 2007, U.S. Provisional Patent Application No. 60/876,128, filed Dec. 21, 2006, and U.S. Provisional Patent Application No. 60/875,606, filed Dec. 19, 2006, the disclosures of which are incorporated herein by reference as if set forth in their entireties.

FIELD OF THE INVENTION

The present invention relates generally to health and environmental monitors and, more particularly, to wireless health and environment monitors.

BACKGROUND OF THE INVENTION

There is growing market demand for personal health and environmental monitors, for example, for gauging overall health and metabolism during exercise, athletic training, dieting, and physical therapy. However, traditional health monitors and environmental monitors may be bulky, rigid, and uncomfortable—generally not suitable for use during daily physical activity. There is also growing interest in generating and comparing health and environmental exposure statistics of the general public and particular demographic groups. For example, collective statistics enable the healthcare industry and medical community to direct healthcare resources to where they are most highly valued. However, methods of collecting these statistics may be expensive and laborious, often utilizing human-based recording/analysis steps at multiple sites.

As such, improved ways of collecting, storing and analyzing personal health and environmental information are needed. In addition, improved ways of distributing raw and analyzed personal health and environmental information are desirable to support efforts to enhance healthcare quality and reduce costs.

SUMMARY

In view of the above discussion, apparatus for monitoring various physiological and environmental factors are provided. According to some embodiments of the present invention, real-time, noninvasive health and environmental monitors include a plurality of compact sensors integrated within small, low-profile devices. Physiological and environmental data is collected and wirelessly transmitted into a wireless network, where the data is stored and/or processed.

In some embodiments of the invention, an earpiece functions as a physiological monitor, an environmental monitor, and a wireless personal communicator. The earpiece can take advantage of commercially available open-architecture wireless paradigms, such as Bluetooth®, Wi-Fi, or ZigBee. In some embodiments, a small, compact earpiece contains at least one microphone and one speaker, and is configured to transmit information wirelessly to a recording device such as, for example, a cell phone, a personal digital assistant (PDA), and/or a computer. The earpiece contains a plurality of sensors for monitoring personal health and environmental exposure. Health and environmental information, sensed by the sensors is transmitted wirelessly, in real-time, to a recording device, capable of processing and organizing the data into meaningful displays, such as charts. In some embodiments, an earpiece user can monitor health and environmental exposure data in real-time, and may also access records of collected data throughout the day, week, month, etc., by observing charts and data through an audio-visual display.

In some embodiments, an earpiece can integrate personal physiological and environmental exposure information with biofeedback and personal entertainment. In other embodiments of the present invention, earpiece monitor devices enable a variety of networks, applications, games, and business methods.

In some embodiments of the present invention, a monitoring apparatus includes a housing configured to be attached to the body of a person, one or more physiological sensors and one or more environmental sensors supported by (within and/or on) the housing. Each physiological sensor is configured to detect and/or measure physiological information from the person, and each environmental sensor is configured to detect and/or measure environmental conditions in a vicinity of the person wearing the apparatus. The apparatus also includes a signal processor that is, configured to receive and process signals produced by the physiological and environmental sensors. A wireless transmitter is responsive to the signal processor and is configured to wirelessly transmit physiological and environmental sensor signals as processed by the signal processor from the signal processor to a remote terminal in real-time.

Each physiological sensor is configured to detect and/or measure one or more of the following types of physiological information: heart rate, pulse rate, breathing rate, blood flow, heartbeat signatures, cardio-pulmonary health, organ health, metabolism, electrolyte type and/or concentration, physical activity, caloric intake, caloric metabolism, blood metabolite levels or ratios, blood pH level, physical and/or psychological stress levels and/or stress level indicators, drug dosage and/or dosimetry, physiological drug reactions, drug chemistry, biochemistry, position and/or balance, body strain, neurological functioning, brain activity, brain waves, blood pressure, cranial pressure, hydration level, auscultatory information, auscultatory signals associated with pregnancy, physiological response to infection, skin and/or core body temperature, eye muscle movement, blood volume, inhaled and/or exhaled breath volume, physical exertion, exhaled breath physical and/or chemical composition, the presence and/or identity and/or concentration of viruses and/or bacteria, foreign matter in the body, internal toxins, heavy metals in the body, anxiety, fertility, ovulation, sex hormones, psychological mood, sleep patterns, hunger and/or thirst, hormone type and/or concentration, cholesterol, lipids, blood panel, bone density, organ and/or body weight, reflex response, sexual arousal, mental and/or physical alertness, sleepiness, auscultatory information, response to external stimuli, swallowing volume, swallowing rate, sickness, voice characteristics, voice tone, voice pitch, voice volume, vital signs, head tilt, allergic reactions, inflammation response, auto-immune response, mutagenic response, DNA, proteins, protein levels in the blood, water content of the blood, pheromones, internal body sounds, digestive system functioning, cellular regeneration response, healing response, stem cell regeneration response Each environmental sensor is configured to detect and/or measure one or more of the following types of environmental information: climate, humidity, temperature, pressure, barometric pressure, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy, optical radiation, X-rays, gamma rays, microwave radiation, terahertz radiation, ultraviolet radiation, infrared radiation, radio waves, atomic energy alpha particles, atomic energy beta-particles, gravity, light intensity, light frequency, light flicker, light phase, ozone, carbon monoxide, carbon dioxide, nitrous oxide, sulfides, airborne pollution, foreign material in the air, viruses, bacteria, signatures from chemical weapons, wind, air turbulence, sound and/or acoustical energy, ultrasonic energy, noise pollution, human voices, animal sounds, diseases expelled from others, exhaled breath and/or breath constituents of others, toxins from others, pheromones from others, industrial and/or transportation sounds, allergens, animal hair, pollen, exhaust from engines, vapors and/or fumes, fuel, signatures for mineral deposits and/or oil deposits, snow, rain, thermal energy, hot surfaces, hot gases, solar energy, hail, ice, vibrations, traffic, the number of people in a vicinity of the person, coughing and/or sneezing sounds from people in the vicinity of the person, loudness and/or pitch from those speaking in the vicinity of the person.

In some embodiments, the signal processor is configured to process signals produced by the physiological and environmental sensors into signals that can be heard and/or viewed by the person wearing the apparatus. In some embodiments, the signal processor is configured to selectively extract environmental effects from signals produced by a physiological sensor and/or selectively extract physiological effects from signals produced by an environmental sensor.

In some embodiments of the present invention, a monitoring apparatus configured to be worn by a person includes a physiological sensor that is oriented in a direction towards the person and an environmental sensor that is oriented in a direction away from the person. A buffer material is positioned between the physiological sensor and environmental sensors and is configured to selectively reflect and/or absorb energy emanating from the environment and/or the person.

In some embodiments of the present invention, a monitoring apparatus may include a receiver that is configured to receive audio and/or video information from a remote terminal, and a communication module that is configured to store and/or process and/or play audio and/or video information received from the remote terminal. In some embodiments, the communication module may be configured to alert (e.g., via audible and/or visible and/or physical alerts) a person wearing the apparatus when a physiological sensor detects certain physiological information from the person and/or when an environmental sensor detects certain environmental information from the vicinity of the person. In some embodiments, the communication module is configured to audibly present vital sign information to the person wearing the apparatus. In some embodiments, the communication module may be configured to store content generated by the person.

In some embodiments of the present invention, a monitoring apparatus may include a transmitter that is configured to transmit signals produced by physiological and environmental sensors associated therewith to a gaming device. The monitoring apparatus may also be configured to receive feedback regarding monitored health and environmental parameters. As such, personal health and environmental feedback can be an active component of a game.

In some embodiments, the apparatus is an earpiece module that is configured to be attached to the ear of a person, and includes a speaker, microphone, and transceiver that is electronically connected to the speaker and microphone and that permits bidirectional wireless communications between the earpiece module and a remote terminal, such as a cell phone. The transceiver (e.g., a Bluetooth®, Wi-Fi, or ZigBee transceiver) is electronically connected to the signal processor and is configured to transmit physiological and environmental sensor signals from the signal processor to the remote terminal. In some embodiments, the earpiece module may include an arm that is attached to the housing and that supports the microphone. The arm may be movable between a stored position and an extended, operative position. The arm may also include one or more physiological sensor and/or environmental sensors.

In some embodiments of the present invention, an earpiece module that is configured to be attached to the ear of a person includes a first acoustical sensor oriented in a direction towards a tympanic membrane of the ear and is configured to detect acoustical energy emanating from the tympanic membrane. A second acoustical sensor is oriented in a direction away from the person. The signal processor is configured to utilize signals produced by the second acoustical signal to extract environmental acoustical energy not emanating from the tympanic membrane from signals produced by the first acoustical sensor. In some embodiments, the earpiece module may include an optical emitter that directs optical energy towards the tympanic membrane, and an optical detector that is configured to detect secondary optical energy emanating from the tympanic membrane. The signal processor is configured to extract selected optical energy from the secondary optical energy emanating from the tympanic membrane. The signal processor may also be configured to extract optical noise from the secondary optical energy emanating from the tympanic membrane. In some embodiments, the optical detector may include a filter configured to pass secondary optical energy at selective wavelengths.

In some embodiments of the present invention, an earpiece module that is configured to be attached to the ear of a person includes an optical detector that is configured to detect acoustically modulated blackbody IR radiation emanating from the tympanic membrane.

In some embodiments of the present invention, an earpiece module that is configured to be attached to the ear of a person includes an optical emitter that directs optical energy towards the tympanic membrane, and an optical detector configured to detect secondary optical energy emanating from the tympanic membrane. In some embodiments, the signal processor may be configured to extract selected optical energy and/or optical noise from the secondary optical energy emanating from the tympanic membrane. In some embodiments, the optical detector may include a filter configured to pass secondary optical energy at selective wavelengths.

In some embodiments of the present invention, an earpiece module that is configured to be attached to the ear of a person includes an ear hook that is configured to attach to an ear of a person. One or more physiological sensors and/or one or more environmental sensors may be supported by the ear hook. In some embodiments, the hook may include a pinna cover that is configured to contact a portion of the pinna of an ear. One or more physiological and/or environmental sensors may be supported by the pinna cover.

In some embodiments of the present invention, an earpiece module may include an arm that extends outwardly therefrom and that supports one or more physiological sensors and/or environmental sensors. For example, the arm may be configured to support physiological sensors configured to detect and/or measure jaw motion and/or arterial blood flow near the neck of a person wearing the earpiece module.

In some embodiments of the present invention, an earpiece module may include an earpiece fitting configured to be inserted near or within the ear canal of a person wearing the earpiece. The earpiece fitting may include one or more physiological sensors configured to detect information from within the ear canal.

In some embodiments of the present invention, an earpiece module may include a transmittance pulse oximeter and/or reflectance pulse oximeter. For example, the earpiece module may include an earlobe clip having a transmittance pulse oximeter and/or reflectance pulse oximeter supported thereby. As another example, the earpiece module may include a transmitter pulse oximeter and/or reflectance pulse oximeter supported at the front or back of the ear.

In some embodiments of the present invention, a monitoring apparatus is an earring. The earring may be configured to operate independently of other monitoring apparatus, such as an earpiece module, or may operate in conjunction with another monitoring apparatus. For example, an earring may include one or more physiological sensors configured to detect and/or measure physiological information from the person, and one or more environmental sensors configured to detect and/or measure environmental conditions in a vicinity of the person wearing the earring. The earring may also include a signal processor that receives and processes signals produced by the physiological and environmental sensors, and a transmitter that transmits physiological and environmental sensor signals from the signal processor to a remote terminal in real-time.

In some embodiments of the present invention, a monitoring apparatus configured to be attached to the ear of a person may include a housing containing one or more physiological and environmental sensors wherein the housing is configured to be positioned in adjacent contacting relationship with the temple of the person.

Monitoring apparatus, according to some embodiments of the present invention, may include various additional devices/features. For example, a monitoring apparatus may include an air sampling system that samples air in a vicinity of the person wearing the apparatus. In some embodiments, one or more physiological sensors in a monitoring apparatus may be configured to detect drowsiness of the person wearing the apparatus. An alarm may be provided that is configured to alert the person in response to one or more physiological sensors detecting drowsiness. In some embodiments, a monitoring apparatus may include a user interface that provides user control over one or more of the physiological and/or environmental sensors. A user interface may be provided on the monitoring apparatus or may be included on a remote device in wireless communication with the monitoring apparatus. In some embodiments, a monitoring apparatus may include a user interface that is configured to allow the person to store a time mark indicating a particular point in time.

Monitoring apparatus, according to some embodiments of the present invention, may be configured to send a signal to a remote terminal when one or more of the physiological and/or environmental sensors are turned off by a user and/or when one or more of the physiological and/or environmental sensors malfunction or fail. In some embodiments, a signal may be sent to a remote terminal when potentially erroneous data has been collected by one or more of the physiological and/or environmental sensors, such as when a person wearing a monitoring apparatus is surrounded by loud noises.

Monitoring apparatus, according to some embodiments of the present invention, may be configured to detect damage to a portion of the body of the person wearing the apparatus, and may be configured to alert the person when such damage is detected. For example, when a person is exposed to sound above a certain level that may be potentially damaging, the person is notified by the apparatus to move away from the noise source. As another example, the person may be alerted upon damage to the tympanic membrane due to loud external noises.

BRIEF DESCRIPTION OF THE DRAWINGS

FIGS. 14A-14B illustrates an earpiece module with an adjustable mouthpiece for monitoring physiological and environmental information near the mouth, according to some embodiments of the present invention, wherein FIG. 14A illustrates the mouthpiece in a stored position and wherein FIG. 14B illustrates the mouthpiece in an extended operative position.

DETAILED DESCRIPTION

Figure 1:
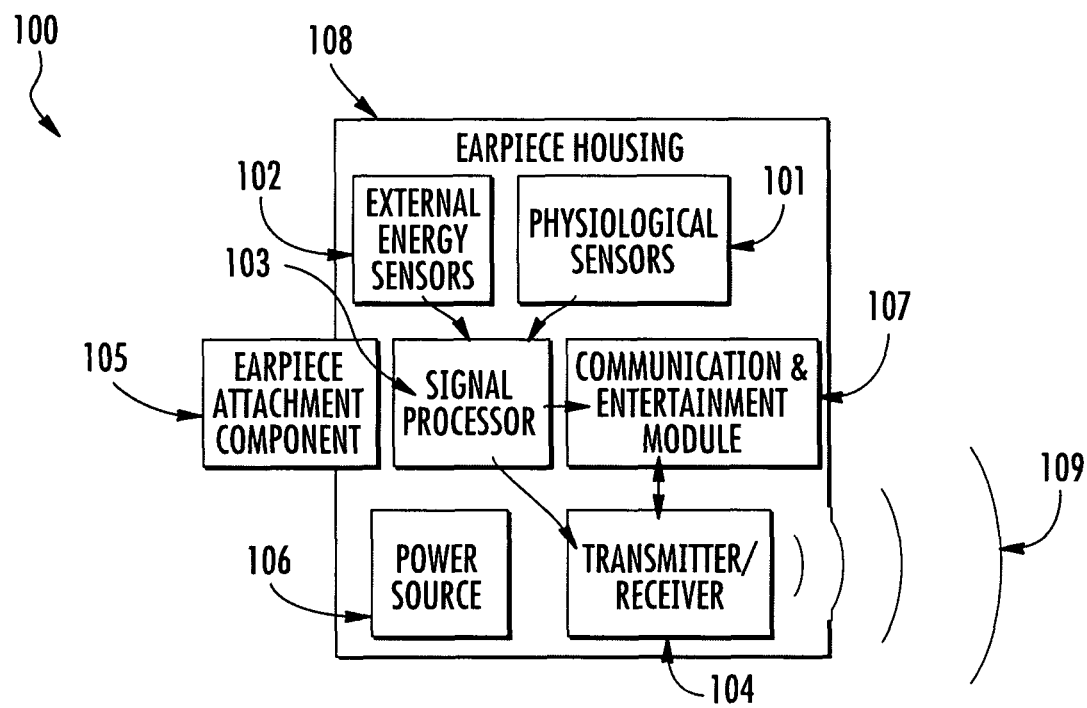
FIG. 1 is a block diagram of a telemetric earpiece module for physiological and environmental monitoring and personal communication, according to some embodiments of the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "earpiece module" includes any type of device that may be attached to or near the ear of a user and may have various configurations, without limitation.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "physiological" refers to matter or energy of or from the body of a creature (e.g., humans, animals, etc.). In embodiments of the present invention, the term "physiological" is intended to be used broadly, covering both physical and psychological matter and energy of or from the body of an organism. However, in some cases, the term "psychological" is called-out separately to emphasize aspects of physiology that are more closely tied to conscious or subconscious brain activity rather than the activity of other organs, tissues, or cells.

The term "psychosocial stress" refers to events of psychological or social origin which challenge the homeostatic state of biological systems.

The term "body" refers to the body of a person (or animal) that may utilize an earpiece module according to embodiments of the present invention. Monitoring apparatus, according to embodiments of the present invention may be worn by humans and animals.

In the following figures, earpiece modules will be illustrated and described for attachment to the ear of the human body. However, it is to be understood that embodiments of the present invention are not limited to those worn by humans. Moreover, monitoring apparatus according to embodiments of the present invention are not limited to earpiece modules and/or devices configured to be attached to or near the ear.

Monitoring apparatus according to embodiments of the present invention may be worn on various parts of the body.

Some embodiments of the present invention may arise from a discovery that the ear is an ideal location on the human body for a wearable health and environmental monitor. The ear is a relatively immobile platform that does not obstruct a person's movement or vision. Devices located along the ear have access to the inner-ear canal and tympanic membrane (for measuring core body temperature), muscle tissue (for monitoring muscle tension), the pinna and earlobe (for monitoring blood gas levels), the region behind the ear (for measuring skin temperature and galvanic skin response), and the internal carotid artery (for measuring cardiopulmonary functioning). The ear is also at or near the point of exposure to: environmental breathable toxicants of interest (volatile organic compounds, pollution, etc.; noise pollution experienced by the ear; and lighting conditions for the eye. Furthermore, as the ear canal is naturally designed for transmitting acoustical energy, the ear provides an optimal location for monitoring internal sounds, such as heartbeat, breathing rate, and mouth motion.

Bluetooth-enabled and/or other personal communication earpiece modules may be configured to incorporate physiological and/or environmental sensors, according to some embodiments of the present invention. Bluetooth earpiece modules are typically lightweight, unobtrusive devices that have become widely accepted socially. Moreover, Bluetooth earpiece modules are cost effective, easy to use, and are often worn by users for most of their waking hours while attending or waiting for cell phone calls. Bluetooth earpiece modules configured according to embodiments of the present invention are advantageous because they provide a function for the user beyond health monitoring, such as personal communication and multimedia applications, thereby encouraging user compliance. Exemplary physiological and environmental sensors that may be incorporated into a Bluetooth or other type of earpiece module include, but are not limited to accelerometers, auscultatory sensors, pressure sensors, humidity sensors, color sensors, light intensity sensors, pressure sensors, etc.

Wireless earpiece devices incorporating low-profile sensors and other electronics, according to embodiments of the present invention, offer a platform for performing near-real-time personal health and environmental monitoring in wearable, socially acceptable devices. The capability to unobtrusively monitor an individual's physiology and/or environment, combined with improved user compliance, is expected to have significant impact on future planned health and environmental exposure studies. This is especially true for those that seek to link environmental stressors with personal stress level indicators. The large scale commercial availability of this low-cost device can enable cost-effective large scale studies. The combination of monitored data with user location via GPS data can make on-going geographic studies possible, including the tracking of infection over large geographic areas. The commercial application of the proposed platform encourages individual-driven health maintenance and promotes a healthier lifestyle through proper caloric intake and exercise.

Accordingly, some embodiments of the present invention combine a personal communications earpiece device with one or more physiological and/or environmental sensor. Other embodiments may combine physiological and/or environmental sensors into an earpiece device.

Embodiments of the present invention are not limited to devices that communicate wirelessly. In some embodiments of the present invention, devices configured to monitor an individual's physiology and/or environment may be wired to a device that stores and/or processes data. In some embodiments, this information may be stored on the earpiece module itself.

FIG. 1 is a block diagram illustrating an earpiece module 100, according to some embodiments of the present invention. The illustrated earpiece module 100 includes one or more of the following: at least one physiological sensor 101, at least one environmental sensor 102 (also referred to as an external energy sensor), at least one signal processor 103, at least one transmitter/receiver 104, at least one power source 106, at least one communication & entertainment module 107, at least one earpiece attachment component 105, and at least one housing 108. Though the health and environmental sensor functionality can be obtained without the communication and entertainment module 107, having this additional module may promote use of the earpiece module 100 by users. The illustrated earpiece module 100 is intended primarily for human use; however, the earpiece module 100 may also be configured for use with other animals having ears sufficient to support an earpiece, such as primates, canines, felines, cattle, and most other mammals.

A physiological sensor 101 can be any compact sensor for monitoring the physiological functioning of the body, such as, but not limited to, sensors for monitoring: heart rate, pulse rate, breathing rate, blood flow, heartbeat signatures, cardiopulmonary health, organ health, metabolism, electrolyte type and concentration, physical activity, caloric intake, caloric metabolism, metabolomics, physical and psychological stress levels and stress level indicators, physiological and psychological response to therapy, drug dosage and activity (drug dosimetry), physiological drug reactions, drug chemistry in the body, biochemistry, position & balance, body strain, neurological functioning, brain activity, brain waves, blood pressure, cranial pressure, hydration level, auscultatory information, auscultatory signals associated with pregnancy, physiological response to infection, skin and core body temperature, eye muscle movement, blood volume, inhaled and exhaled breath volume, physical exertion, exhaled breath physical and chemical composition, the presence, identity, and concentration of viruses & bacteria, foreign matter in the body, internal toxins, heavy metals in the body, anxiety, fertility, ovulation, sex hormones, psychological mood, sleep patterns, hunger & thirst, hormone type and concentration, cholesterol, lipids, blood panel, bone density, body fat density, muscle density, organ and body weight, reflex response, sexual arousal, mental and physical alertness, sleepiness, auscultatory information, response to external stimuli, swallowing volume, swallowing rate, sickness, voice characteristics, tone, pitch, and volume of the voice, vital signs, head tilt, allergic reactions, inflammation response, auto-immune response, mutagenic response, DNA, proteins, protein levels in the blood, body hydration, water content of the blood, pheromones, internal body sounds, digestive system functioning, cellular regeneration response, healing response, stem cell regeneration response, and the like. Vital signs can include pulse rate, breathing rate, blood pressure, pulse signature, body temperature, hydration level, skin temperature, and the like. A physiological sensor may include an impedance plethysmograph for measuring changes in volume within an organ or body (usually resulting from fluctuations in the amount of blood or air it contains). For example, the earpiece module 100 may include an impedance plethysmograph to monitor blood pressure in real-time.

An external energy sensor 102, serving primarily as an environmental sensor, can be any compact sensor for monitoring the external environment in the vicinity of the body, such as, but not limited to, sensors for monitoring: climate, humidity, temperature, pressure, barometric pressure, pollution, automobile exhaust, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy (optical radiation, X-rays, gamma rays, microwave radiation, terahertz radiation, ultraviolet radiation, infrared radiation, radio waves, and the like), EMF energy, atomic energy (alpha particles, beta-particles, gamma rays, and the like), gravity, light properties (such as intensity, frequency, flicker, and phase), ozone, carbon monoxide, greenhouse gases, $CO_2$, nitrous oxide, sulfides, airborne pollution, foreign material in the air, biological particles (viruses, bacteria, and toxins), signatures from chemical weapons, wind, air turbulence, sound and acoustical energy (both human audible and inaudible), ultrasonic energy, noise pollution, human voices, animal sounds, diseases expelled from others, the exhaled breath and breath constituents of others, toxins from others, bacteria & viruses from others, pheromones from others, industrial and transportation sounds, allergens, animal hair, pollen, exhaust from engines, vapors & fumes, fuel, signatures for mineral deposits or oil deposits, snow, rain, thermal energy, hot surfaces, hot gases, solar energy, hail, ice, vibrations, traffic, the number of people in a vicinity of the user, the number of people encountered throughout the day, other earpiece module users in the vicinity of the earpiece module user, coughing and sneezing sounds from people in the vicinity of the user, loudness and pitch from those speaking in the vicinity of the user, and the like.

In some embodiments, a physiological sensor 101 and/or an environmental sensor 102 may be configured to identify a person to whom the earpiece module 100 is attached.

In some embodiments, a physiological sensor 101 and/or an environmental sensor 102 may be configured to monitor physical aging rate of a person or subject. The signal processor 103 may be configured to processes information from a physiological sensor and/or an environmental sensor to assess aging rate. Physiological sensors configured to assess aging rate may include pulse rate sensors, blood pressure sensors, activity sensors, and psychosocial stress sensors. Environmental sensors configured to assess aging rate may include UV sensors and pollution sensors.

In some embodiments, a physiological sensor 101 and/or an environmental sensor 102 may be configured to be regenerated through a physical and/or chemical change. For example, it is anticipated that an earpiece module 100, or other device incorporating physiological and/or environmental sensors according to embodiments of the present invention may be coupled to an apparatus that is configured to "recharge" or regenerate one or more environmental and/or physiological sensors via a physical process or a chemical process, etc.

Because the earpiece module is capable of measuring and transmitting sensor information in real-time over a duration of time, the physiological and environmental sensors 101, 102 can be used to sense the aforementioned parameters over time, enabling a time-dependent analysis of the user's health and environment as well as enabling a comparison between the user's health and environment. Combined with proximity or location detection, this allows an analysis for pinpointing the location where environmental stress and physical strain took place. The signal processor 103 provides a means of converting the digital or analog signals from the sensors 101, 102 into data that can be transmitted wirelessly by the transmitter 104. The signal processor 103 may be composed of, for example, signal conditioners, amplifiers, filters, digital-to-analog and analog-to-digital converters, digital encoders, modulators, mixers, multiplexers, transistors, various switches, microprocessors, or the like. For personal communication, the signal processor 103 processes signals received by the receiver 104 into signals that can be heard or viewed by the user. The received signals may also contain protocol information for linking various telemetric modules together, and this protocol information can also be processed by the signal processor 103. The signal processor 103 may utilize one or more "compression/decompression algorithms used in digital media" (CODECs) for processing data. The transmitter 104 can be comprised of a variety of compact electromagnetic transmitters. A standard compact antenna is used in the standard Bluetooth headset protocol, but any kind of electromagnetic antenna suitable for transmitting at human-safe electromagnetic frequencies may be utilized. The receiver 104 can also be an antenna. In some embodiments, the receiving antenna and the transmitting antenna are physically the same. The receiver/transmitter 104 can be, for example, a non-line-of-sight (NLOS) optical scatter transmission system. These systems typically use short-wave (blue or UV) optical radiation or "solar blind" (deep-UV) radiation in order to promote optical scatter, but IR wavelengths can also suffice. Additionally, a sonic or ultrasonic transmitter can be used as the receiver/transmitter 104 of the earpiece module 100, but preferably using sounds that are higher or lower than the human hearing range. A variety of sonic and ultrasonic receivers and transmitters are available in the marketplace and may be utilized in accordance with embodiments of the present invention. If a telecommunication device 210 (FIG. 2) receiving wireless data signal 109 from the earpiece module 100 is in close proximity to the earpiece module, a variety of transmission schemes can be used. For communicating audible conversational information directly to the earpiece user, encoded telemetric conversational data received by the receiver 104 can be decoded by the signal processing module 103 to generate an electrical signal that can be converted into audible sound by the communication module 107.

In some embodiments, the transmitter/receiver 104 is configured to transmit signals from the signal processor to the remote terminal following a predetermined time interval. For example, the transmitter may delay transmission until a certain amount of detection time has elapsed, until a certain amount of processing time has elapsed, etc.

The power source can be any portable power source 106 capable of fitting inside the earpiece module housing. According to some embodiments, the power source 106 is a portable rechargeable lithium-polymer or zinc-air battery. Additionally, portable energy-harvesting power sources can be integrated into the earpiece module 100 and can serve as a primary or secondary power source. For example, a solar cell module can be integrated into the earpiece module 100 for collecting and storing solar energy. Additionally, piezoelectric devices or microelectromechanical systems (MEMS) can be used to collect and store energy from body movements, electromagnetic energy, and other forms of energy in the environment or from the user himself. A thermoelectric or thermovoltaic device can be used to supply some degree of power from thermal energy or temperature gradients. In some embodiments, a cranking or winding mechanism can be used to store mechanical energy for electrical conversion or to convert mechanical energy into electrical energy that can be used immediately or stored for later.

The various components describe above are configured to fit within the earpiece housing 108 and/or be attached thereto. The earpiece module housing 108 may be formed from any safe and comfortable solid material, such as metal, rubber, wood, polymers, ceramic, organic materials, or various forms of plastic. The earpiece attachment component 105 is attached to the earpiece module housing 108 and is designed to fit around or near the ear. For example, the standard Bluetooth headset includes an earpiece attachment that is connected to the headset housing via a double-jointed socket, to provide comfort and positioning flexibility for the user. In some embodiments, the earpiece attachment component 105 can be part of the housing 108, such that the entire earpiece module is one largely inflexible, rigid unit. In such case, a counterweight may be incorporated into the earpiece module 100 to balance the weight of the earpiece electronics and power source. In some embodiments, the earpiece attachment component 105 can contain physiological and environmental sensors, and the earpiece attachment component 105 may be detachable. In some embodiments, more than one earpiece attachment 105 can be attached to the earpiece module housing 108.

Figure 2:
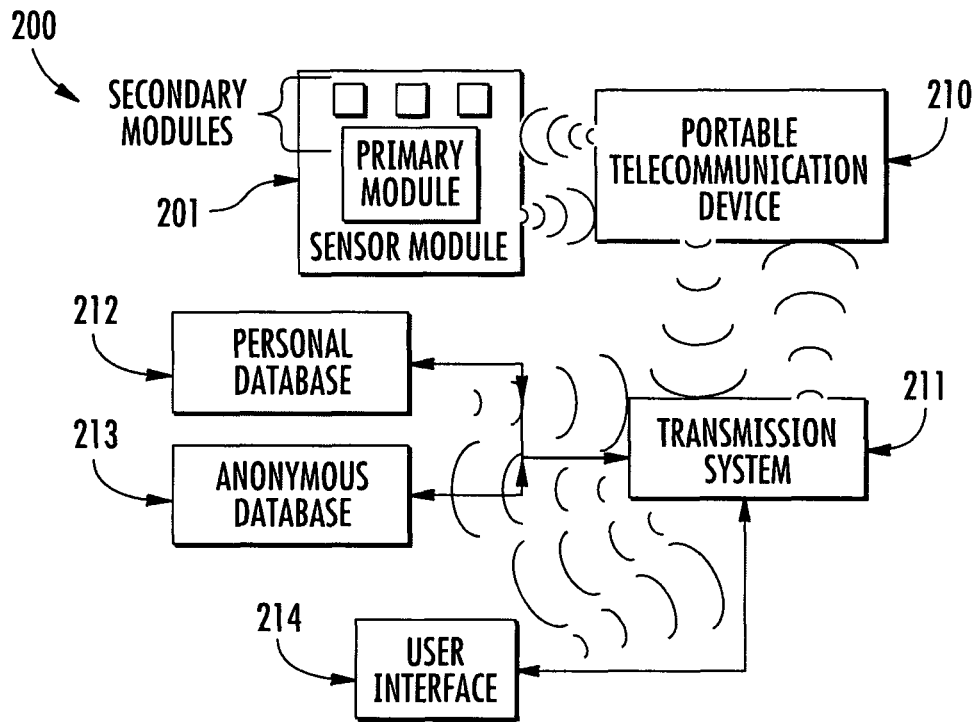
FIG. 2 is a block diagram of a telemetric network for health and environmental monitoring through portable telemetric sensor modules, such as the earpiece module of FIG. 1, according to some embodiments of the present invention.

The communication and entertainment module 107 (also interchangeably referred to as a "communication module") is used for, but not limited to: processing or generating an audible sound from information received via the receiver 104 (from a cell phone, computer, network, database, or the like) and/or processing or generating an electrical signal from an audible sound from the user such that the electrical signal can be transmitted telemetrically via the transmitter 104. For example, in standard Bluetooth protocol, communication electronics are used to convert an audible conversation into an electrical signal for telemetric conversation; communication electronics are also used to convert a digitized telemetric conversation into an audible conversation for the earpiece user. Additionally, the communication and entertainment module 107 can be used to store, process, or play analog or digital information from music, radio shows, videos, or other audible entertainment and to communicate this information to an earpiece user. In many cases, this information includes information received by the receiver 104. In many cases, the analog or digital information is not stored in the communication and entertainment module 107 but, rather, is stored in a portable telecommunication device 210 (FIG. 2). In such case, the communication and entertainment module 107 is used for converting the analog or digital information into audible sound for the earpiece user. The communication and entertainment module 107 may contain at least one microphone, speaker, signal processor (similar to 103), and digital memory. In some embodiments, the communication and entertainment module 107 may apply at least one CODEC for encoding or decoding information. The communication and entertainment module may utilize non-audible forms of communication with the user, such as visual, physical, or mental (i.e., brainwaves or neural stimulation) communication with the user.

In some embodiments, an audible communicator is provided that is configured to communicate therapeutic sounds (e.g., music therapy, etc.) to the person in response to physiological or psychosocial stress. The audible communicator may be embodied in the communication and entertainment module 107 or may be a separate speaker. In some embodiments, light therapy may be provided to the person in response to physiological or psychosocial stress. In some embodiments, the communication and entertainment module 107 may be configured to communicate a treatment, therapy, and/or plan of action to the person upon detection of physiological and/or environmental concerns. For example, if it is detected that the person is being exposed to unhealthy doses of UV radiation, the communication and entertainment module 107 may audibly instruct the person to move away from the person's current location (e.g., move indoors, etc.).

Like the other components of the earpiece module 100 shown in FIG. 1, the components of the communication and entertainment module 107 are not necessarily located in the same physical vicinity. The microphone and speaker of the communication module 107, for example, are located closer to the mouth and ear respectively. Furthermore, the signal processor 103 can be composed of several components located throughout the earpiece module. It should be understood that the word "module" does not necessarily imply a unified physical location. Rather, "module" is used to imply a unified function.

Bluetooth devices conventionally contain a communication module, such as communication module 107, for converting digital or analog information into audible sounds for the user. However, when combined with the health and environmental monitoring properties of an earpiece module 100 according to embodiments of the present invention, the communication and entertainment module 107 can provide functionality. For example, the earpiece module can serve as a biofeedback device. As a non-limiting example, if a user is in a polluted environment, such as air filled with VOCs, the communication module 107 may notify the user to move to a new environment. As another example, if one or more of the physiological and environmental sensors 101, 102 of the earpiece module 100 pick up a high particulate density in the environment, with an elevation in core body temperature, and a change in voice pitch occurring simultaneously (or near-simultaneously) within a common timeframe, the communication module 107 may alert the user that he/she may be having an allergic response. As a further example, the user can use the communication and entertainment module 107 to execute biofeedback for willfully controlling blood pressure, breathing rate, body temperature, pulse rate, and the like. The communication module 107 may utilize audible or visible alerts if the user is meeting their physiological targets or exceeding safe physiological limits. Alerting a user by physical or electrical force, such as the sense of touch or tingling from an electric pulse or vibration, can also be utilized. Thus, although communication by audible means is often utilized, the communication module 107 can alert, signify, or communicate with the user through sound, light, electrical actuation, and physical actuation.

As a second example of this biofeedback method, basic vital signs collected by the physiological sensors 101 and processed by the signal processor 103 can be presented to the earpiece user audibly, through the communication and entertainment module 107. For example, the user may be able to listen to his/her breathing rate, pulse rate, and the like. Additionally, an entertaining or aggravating sound or song can be used to alert the user to favorable or unfavorable personal health and environmental factors occurring in real-time. This technique may be applied towards education, such as positive or negative feedback for educational games, learning games, or games of deception (e.g., poker, etc.).

In some embodiments, the earpiece module 100 may be configured to deliver and/or monitor drugs. For example, a transdermal drug delivery system may be provided that is controlled by earpiece electronics. Earpiece sensors can monitor the drug dosage and the physiological effects of the drug in real-time.

A health and environmental network 200 according to embodiments of the present invention that may incorporate the earpiece module 100 of FIG. 1 is illustrated in FIG. 2. The earpiece module 100 is a specific sensor module 201 of the network 200, though other modules located at various other parts of the body can be used in conjunction with, or in place of, the earpiece module 100. The terms "earpiece module 100" and "sensor module 200" are used interchangeably herein in accordance with various embodiments of the present invention. The health and environmental network 200 is composed of at least one sensor module 201 (e.g., earpiece module 100) at least one portable telecommunication module 210, at least one transmission system 211, at least one user interface 214, at least one personal database 212, and at least one anonymous database 213.

The sensor module 201 can be composed of a primary module alone or a primary module and at least one secondary module. The secondary modules can be located at any location of the body, but are preferably located in a region near the ear, and preferably the earpiece module 100 serves as the primary module. In most cases, the secondary modules are not necessary. But in some cases, secondary modules may be located, for example, behind the ear (near the lymph nodes), at or near the earlobes (such as one or more earrings or ear clips), at the front of the ear (near the carotid artery), at the temples, along the neck, or other locations near the ear. These wearable secondary modules can be connected with either a "hard" connection to the primary module (such as an electric cable) or a "soft" connection to the primary module (such as a wireless connection). In Bluetooth protocol, each secondary module can be simultaneously in direct wireless communication with the primary module. Primary modules and secondary modules in the same location can promote quick-donning, ease-of-use, and comfortability for the end user. Users are not prone to accept multiple modules at multiple locations of the body.

The earpiece sensor module 201 communicates wirelessly with the portable telecommunication device 210, preferably in an open architecture configuration, such as Bluetooth or ZigBee. The telecommunication device 210 can be any portable device, such as a cell phone, PDA, laptop computer, Blackberry, another earpiece, or other portable, telemetric device. The portable telecommunication device 210 and the earpiece module 201 can telemetrically communicate both to and from each other. Though the main purpose of the portable telecommunication device is to transmit the local wireless signal from the sensor module 101 over longer distances unattainable by the transmitter 104 of the sensor module 201, the telecommunication 210 can also serve as a method of personal communication and entertainment for the earpiece user.

In some embodiments, the telecommunication device 210 transmits data in only one direction or particular directions. For example, in one embodiment, the portable telecommunication device 210 can receive telemetric information from the sensor module 201 but cannot send out signals to a transmission system 211. The portable telecommunication device 210 may also contain an end-user graphical interface, such as a user interface 214 in the network 200, such that data from the earpiece module 201 can be stored, analyzed, summarized, and displayed on the portable telecommunication device 210. For example, charts relating health and environment, as well as real-time biofeedback and the like, can be displayed on a cell phone, media player, PDA, laptop, or other device. The telecommunication device 210 may also contain physiological and environmental sensors itself, such as blood pressure, pulse rate, and pulse-oximetry, and the like. Additionally, the telecommunication device 210 can communicate with the earpiece module 201 to transfer commands, activate or deactivate sensors, communicate with the user, and the like.

The portable telecommunication device 210 sends/receives wireless information directly to/from a transmission system 211 for transmission to a database (such as personal database 312 and/or anonymous database 313) for storage, analysis, and retrieval of data. The style of transmission system depends largely on the location of the database. For example, if the database is located in a local computer, the wireless information from the telecommunication device 210 can be sent directly to the local computer. This computer may be connected with the Internet, allowing access to the database from the web. However, the database is more typically located far away from the user and telecommunication module. In this case, the wireless signal from the telecommunication device 210 can be sent to a reception tower and routed through a base station. This information can then be sent to a database through the Internet. A variety of other transmission protocols can be applied for connection between the telecommunication device 210 and the databases 212, 213.

The personal and anonymous databases 212, 213 represent databases that may or may not be located on the same computer. A key difference between these two databases is not the physical location of the database but rather the type of information available on each database. For example, the anonymous database 213, containing health and environmental data from multiple indistinct earpiece users, can be public and accessible through the Internet by various users. In contrast, the personal database 212 contains health and environmental data that is personalized for each user, including personalized information such as name, birth date, address, and the like. Users can log-in to their personalized information in the personal database 212 through an interactive user interface 214 and compare this information with information from multiple users in the anonymous database 213 via a graphical user interface.

The user interface 214 can be a computer monitor, a cell phone monitor, a PDA monitor, a television, a projection monitor, a visual monitor on the earpiece module 201, or any method of visual display. (Audible methods and audio-visual methods can also be used for the user interface 214.) For example, the user may log-in to their personal database 212 through a computer user interface 214 and compare real-time personal health and environmental exposure data with that of other users on the network 200. In some cases, the data from other users may be anonymous statistics. In some cases, one or more users may have agreements to view the data of one or more other users, and in other cases, users may agree to share mutual personalized data through the Internet.

Figure 3:
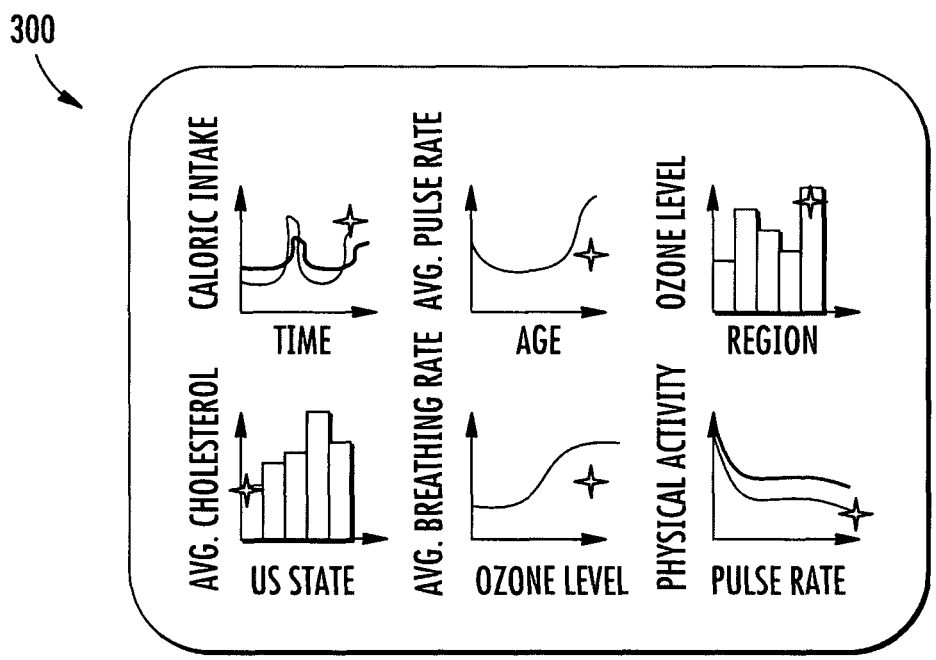
FIG. 3 illustrates a graphical user interface for displaying data, according to some embodiments of the present invention.

A specific embodiment of a graphical user interface 300 is presented in FIG. 3. FIG. 3 shows an example of how a computer monitor may appear to a user logging-in to their personal database 212 and comparing their own personal data with that of anonymous users in the same network 200. In this case, data from anonymous users is averaged into certain demographics; the choice of the demographics to be displayed can be selected by the user accessing the personalized database. In the graphical user interface 300 of FIG. 3, the user's personalized data, signified by a star, is compared with statistics from other users in an anonymous database 213. This allows the user to compare his/her health and environment with that of others in selected demographics. Thus, this network 200 serves not only as a source of useful information from a medical standpoint, but also as a form of entertainment for curious users.

The network 200 can be used in medicine for a variety of important functions. As one example, a doctor can monitor the health of patients through each patient's personalized database 212. If the earpiece module 201 contains a dosimeter, the doctor can even monitor the efficacy of prescribed medications, and the physiological response to medications, over time. This dosimetry approach is directly applicable to clinical studies of various treatments. For example, during a clinical trial, the earpiece module 201 can collect environmental data, drug dosimetry data, and physiological data from the earpiece user such that researchers can understand the etymology between drugs, genes, physiology, environment, and personal health.

Because of the high compliance of the earpiece module 100, primarily due to the dual-modality as a health/environmental monitor and a personal communication/entertainment device, users are prone to wear this device throughout clinical trials, providing more valuable information for drug discovery and the pharmaceuticals market.

As a further example, the health and environmental network 200 can be used by dieticians to track the caloric intake, health, and physical activity of dieters. Similarly, the network 200 can be used by athletic trainers to monitor the diet, physical activity, health, and environment of athletes. In many cases professionals are not necessary, and the user can monitor his/her own diet, activity, athletic performance, etc. through the network without professionals; parents, guardians, or friends monitoring their personal statistics.

In a specific example of the network 200, an earpiece user is a test subject in a clinical trial for a new treatment, such as a new drug, physical therapy, medical device, or the like. The earpiece user's health and environment are monitored in realtime, and this data is stored on the earpiece module 201, the portable telecommunication device 210, the personal database 212, or the anonymous database 213. By accessing the stored data, researchers managing the clinical trial can then compare the statistics from multiple users to make correlations between user environment, health, and the effectiveness of treatment.

It should be noted that algorithms for processing personal health and environmental data, diagnosing medical conditions, assessing health states, and the like do not need to be limited to the illustrated network 200. Various algorithms can also be integrated into the earpiece module 201 or telecommunication device 210 according to embodiments of the present invention. A data storage component in at least one of these units allows processed signal data to be stored, analyzed, and manipulated to provide new knowledge to the user. This storage component can be any solid-state storage device, such as flash memory, random-access memory (RAM), magnetic storage, or the like. For example, the earpiece module 201 can be programmed to monitor certain habits, such as nail-biting. In this non-limiting example, the earpiece module physiological sensors 101 may monitor internal sounds, and an algorithm can be implemented to monitor signatures of nail-biting sounds in real-time. If the habit is identified by the algorithm, the earpiece communication module 107 may instantly warn the user that the habit is occurring. Alternatively, the algorithm may count the number of times a day the habit occurred, monitor physiological and psychological stress indicators during each occurrence, log each time when the habit occurred, and store environmental data associated with the habit. This stored data can be accessed at a later time, allowing the user to determine what environmental factors cause the physiological or psychological stress associated with nail-biting. As this example shows, these algorithms can take advantage of both physiological sensor 101 data and environmental sensor 102 data.

A data storage component may include various algorithms, without limitation. In some embodiments, at least one algorithm is configured to focus processing resources on the extraction of physiological and/or environmental information from the various environmental and/or physiological sensors. Algorithms may be modified and/or uploaded wirelessly via a transmitter (e.g., receiver/transmitter 104 of the earpiece module 100)

The biofeedback functionality of the telemetric earpiece module 100 can be applied towards various gaming applications. For example, one or more earpiece users can connect their earpiece modules 100 to one or more gaming devices wirelessly through the open architecture network provided by Bluetooth, ZigBee, or other such networks. This allows personal health and environmental information to be transferred wirelessly between the earpiece module 100 and a gaming device. As earpiece users play a game, various personal health and environmental feedback can be an active component of the game. In a non-limiting embodiment, two users playing a dancing game, such as Dance Dance Revolution, can monitor their vital signs while competing in a dancing competition. In some cases, users having healthier vital signs, showing improved athletic performance, will get extra points ("Vital Points"). In another specific example, this personal health and environmental information can be sent telemetrically to a gaming device to make entertaining predictions about one or more users. Namely, the gaming device may predict someone's life expectancy, love-life, future occupation, capacity for wealth, and the like. These predictions can be true predictions, purely entertaining predictions, or a mixture of both. Sensors measuring external stressors (such as outside noise, lighting conditions, ozone levels, etc.) and sensors measuring internal stresses (such as muscle tension, breathing rate, pulse rate, etc.) integrated into the earpiece module 100 can be used to facilitate predictions by the gaming device. For example, the information from the sensors can be recorded from one or more earpiece users during a series of questions or tasks, and the information can be sent telemetrically to a gaming device. An algorithm processed in the gaming device can then generate an entertaining assessment from the information. This game can be in the form of a video game, with a graphical user interface 214, or it can be a game "in person" through an entertainer. Other games can involve competitions between multiple earpiece monitor users for health-related purposes, such as online dieting competitions, fitness competitions, activity competitions, or the like. Combining the telemetric earpiece module 100 with gaming, according to embodiments of the present invention, provides seamless interaction between health and environmental monitoring and the game, through a comfortable telemetric module. Other sensor modules 201 located at other parts of the body can also be used.

An additional non-limiting embodiment of the biofeedback functionality of the earpiece module 201 can be monitoring psychological and physiological stress (such as monitoring stress indicators) during a poker game. These stress indicators can be breathing rate, muscle tension, neurological activity, brain wave intensity and activity, core body temperature, pulse rate, blood pressure, galvanometric response, and the like. Users may, for example, use the earpiece module 201 to record or display their psychological and physiological stress during a poker game in real-time. This information can be stored or displayed on a portable telecommunication device 210 or sent wirelessly to other parts of the network 200. The user can use this biofeedback to adjust their psychological and physiological stress (or stress indicators) through force of will. This biofeedback process allows earpiece users to self-train themselves to project a certain "poker face," such as a stoic cold look, a calm cool look, or another preferred look. Additionally, external stressors, such as light intensity and color, external sounds, and ambient temperature, can be sensed, digitized, and transmitted by the earpiece module 100 to a telecommunication device (for storage), providing the user with important information about how the external environment may be affecting their stress response and, hence, poker game. In some games, the stress indicators may be displayed for outside viewers (who are not part of the poker game) as a form of entertainment when watching a group of poker players (each having earpiece modules 201) in a casino, television, or through the Internet.

The biofeedback approach is also directly relevant to personal education as a learning tool. For example, monitoring the physiological and psychological response to learning can be used to help users understand if they are learning efficiently. For example, in the course of reading, the earpiece module 201 can monitor alertness through galvanometric, brainwave, or vital sign monitoring. The user can then use this information to understand what reading methods or materials are stimulating and which are not stimulating to the earpiece user.

In the broader sense, the discussed earpiece-enabled biofeedback method can be used as a self-training tool for improving performance in public speaking, athletic activity, teaching, and other personal and job-related activities.

The health and environmental network 200 enables a variety of additional business methods. For example, users can be charged a fee for downloading or viewing data from the personal and/or anonymous databases 212, 213. Alternatively, users may be allowed free access but be required to register online, providing personal information with no restrictions on use, for the right to view information from the databases. In turn, this personal information can be traded or sold by the database owner(s). This information can provide valuable marketing information for various companies and government interests. The health and environmental data from the databases 212, 213 can be of great value itself, and this data can be traded or sold to others, such as marketing groups, manufacturers, service providers, government organizations, and the like. The web-page or web-pages associated with the personal and anonymous databases 212, 213 may be subject to targeted advertising. For example, if a user shows a pattern of high blood pressure on a personal database 212, a company may target blood pressure treatment advertisements on the user interface 214 (i.e. web page) while the user is logged-in to the personal database through the user interface 214. For example, because various health and environmental statistics of earpiece users will be available on the database, this information can be used to provide a targeted advertising platform for various manufacturers. In this case, a database manager can sell information to others for targeted advertising linked to a user's personal statistics. In some cases, a database owner does not need to sell the statistics in order to sell the targeted advertising medium. As a specific example, a company can provide a database owner with statistics of interest for targeted advertising. For example, the company may request advertising a weight-loss drug to anonymous users having a poor diet, high caloric intake, and/or increasing weight. A database manager can then charge the company a fee for distributing these advertisements to the targeted users as they are logged-in to the database website(s). In this way, the users remain anonymous to the company. Because targeted advertisements can be such a lucrative market, income from these sources may eliminate the need for charging users a fee for logging-in to the databases 212, 213.

The earpiece module 201 and earpiece module network 200 can enable a variety of research techniques. For example, a plurality of earpiece modules 100 worn by users can be used in marketing research to study the physiological and psychological response of test subjects to various marketing techniques. This technique solves a major problem in marketing research: deciphering objective responses in the midst of human subjectivity. This is because the physiological and psychological response of the earpiece user largely represents objective, unfiltered information. For example, users that are entertained by a pilot TV program would have difficulty hiding innate vital signs in response to the program. The data generated by the earpiece module 201 during market research can be transmitted through any component of the telemetric network 200 and used by marketing researchers to improve a product, service, or method.

Another business method provided by the network 200 is to charge users of the network for usage and service (such as compilation service). For example, a clinical trial company may pay a fee for accessing the databases 212, 213 of their test subjects during medical research. In this case, these companies may buy earpiece modules 201 and pay for the service, or the earpiece modules 201 may be provided free to these companies, as the database service can provide a suitable income itself. Similarly, doctors may pay for this service to monitor patients, fire fighters and first responders may pay for this service to monitor personnel in hazardous environments, and athletic trainers may pay for this service to monitor athletes. Also, users can pay for the database service directly themselves. Because these databases 212, 213 are dynamic, updated regularly via the earpiece module 201 of each user, and changing with time for individual users and users en mass, these databases can maintain a long-term value. In other words, there may always be new information on the databases 212, 213.

Another embodiment of the present invention involves methods of combining information from various earpiece health sensors into a meaningful real-time personal health and environmental exposure assessment in a recording device. The meaningful assessment is generated by algorithms that can be executed in the earpiece 201, in the portable telecommunication device 210, or through various other electronic devices and media within the network 200. In one embodiment, raw or preprocessed data from the sensor module 201 is transmitted wirelessly to the telecommunication device 210, and this device executes various algorithms to convert the raw sensor data (from one or more sensors) into a meaningful assessment for the user. In another embodiment these algorithms are executed within the earpiece 201 itself, without the need for processing in the telecommunication device 210. The output from these algorithms can be viewed as charts, graphs, figures, photos, or other formats for the user to view and analyze. Preferably, these formats display various health factors over time with respect to a particular environment, with health factor intensity on the dependent axis and time or environmental factor intensity on the independent axis. However, virtually any relationship between the physiological data and environmental data can be processed by the algorithm, and these relationships can be quantitative, qualitative, or a combination of both.

One innovation involves applying the earpiece sensor module 201 towards a physical or mental health assessment method. An algorithm may combine data from health and environmental sensors 101, 102 towards generating a personal overall health assessment for the user, conditional to a particular environment. For example breathing rate, pulse rate, and core body temperature can be compared with ozone density in the air for generating an ozone-dependent personal health assessment. In another specific example of this innovation, information from the earpiece sensors 101, 102 can be used to monitor overall "mood" of a user in a particular environment. More particularly, algorithmic processing and analyzing of data from sensors for core body temperature, heart rate, physical activity, and lighting condition can provide a personal assessment of overall mood conditional on external lighting conditions.

As previously mentioned, the ear is located at an ideal physiological position for monitoring a variety of health and environmental factors. Thus, the ear location can enable a variety of methodologies for physiological and environmental monitoring with an earpiece module 100. In particular, because the ear canal is naturally designed for the transmission of audible sound, the ear canal facilitates methods for monitoring physiological processes by monitoring internal sounds. However, when extracting physiological information from the body, in a given external environment, environmental information is inevitably part of the extracted signal. This is because external energy, such as external audible noise, is entering the body. Thus, when listening to internal sounds, external sounds are also picked up. A methodology for cleaning up the signal such that it contains clearer information about physiology (as opposed to external environment) is provided by some embodiments of the present invention.

Figures 4, 5:
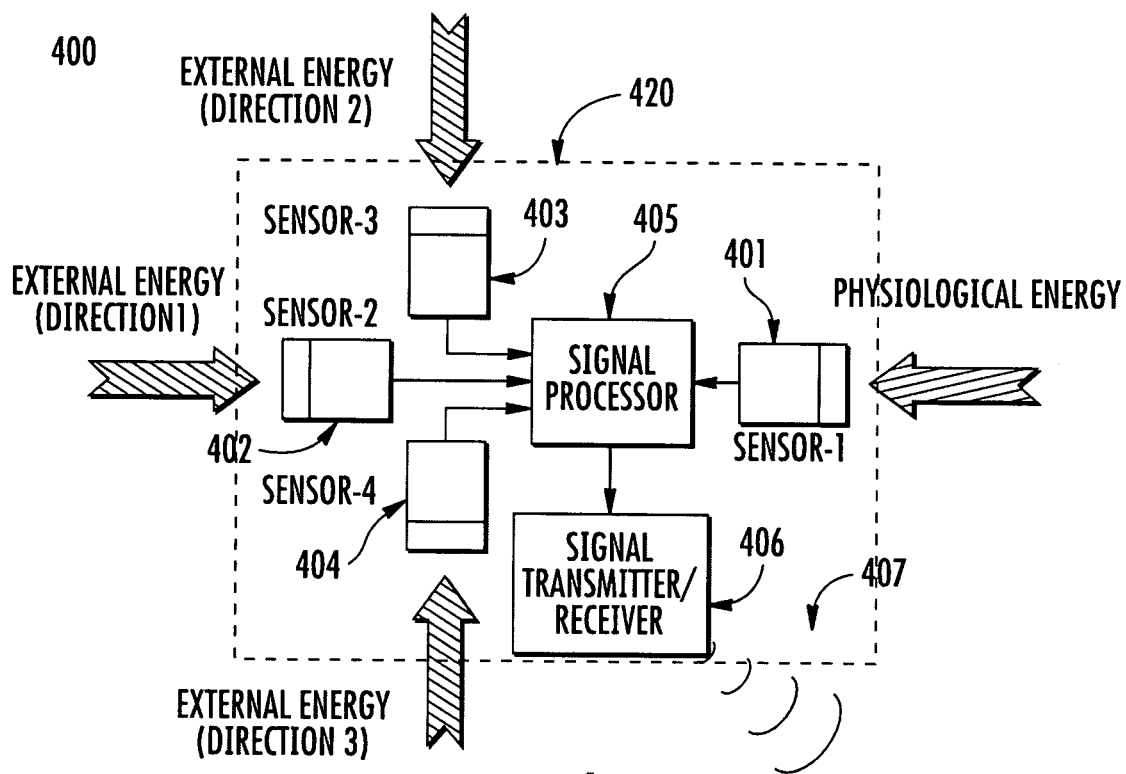
FIG. 4 is a block diagram that illustrates a method of extracting physiological and environmental information using a plurality of sensors and a signal processor, according to some embodiments of the present invention.
FIG. 5 illustrates an auscultatory signal extraction technique according to the methodology illustrated in FIG. 4.

FIG. 4 illustrates a physiological signal extraction methodology 400 for selectively monitoring internal physiological energies through an earpiece module 420 according to embodiments of the present invention. In the illustrated method, internal physiological energy is sensed by a sensor designated "Sensor-1" 401. Sensor-1 generates an electrical signal in response to the physiological energy. One or more external sensors 402, 403, and 404 sense external energy from the environment in the vicinity of the earpiece module user and generate an electrical signal in response to the external energy. Though only one external sensor is needed, multiple sensors can be used to add sensing functionality, improve signal extraction, and/or increase the selectivity of sensing various energies. In FIG. 4, the external energy sensors 402, 403, 404 are shown collecting energy from different directions to emphasize that each sensor can be sensing the same type of energy but from a different direction, as this directional information can be useful for various assessments of the earpiece user. The energies described can be any physical energy, such as electrical, magnetic, electromagnetic, atomic, gravity, mechanical, acoustic, and the like. A signal processor 405 collects the electrical sensor responses and processes these signals into a signal that can be transmitted wirelessly through a transmitter/receiver 406 for communicating the information 407 telemetrically between the earpiece module 420 and a portable telecommunication device 210 (FIG. 2).

As with processor 103 of FIG. 1, the signal processor 405 of FIG. 4 can be used to combine signals from the various sensors, compare similarities between the signals, and generate a new signal that contains cleaner physiological information than any of the original signals. This can be done by converting the analog signals from the physiological sensors 401 and environmental sensors 402, 403, and 404 into digital signals and comparing the signals in, for example, a digital comparator to form a new signal that contains cleaner physiological information. (In some cases, an analog comparator technique can also be used if the signals are not digitized.) If these digitized signals are synchronized in time, a subtraction of environmental features from the signals can be realized by the comparator. Further, if algorithms are integrated into the signal processor 405, comparisons can be made with respect to how external energy affects physiological energy in time.

An embodiment of the physiological signal extraction methodology 400 is presented in FIG. 5 as an acoustical-cancellation physiological signal extraction methodology 500. An earpiece module 517 (for example, with the functionality of earpiece module 100 of FIG. 1) is attached to the ear 506 with an ear attachment 505. This earpiece module 517 is physically similar, if not identical, to the various examples shown in FIGS. 9-16, discussed below. The earpiece module 517 contains at least one physiological acoustical sensor 501 pointed in the direction of the tympanic membrane 520 and at least one external acoustical sensor 502 pointing away from the body and towards the outside environment. To suppress the convolution of external and internal sounds, an acoustical buffer region 519 is placed between the two sensors 501, 502. Environmental sounds 507 are sampled by the external acoustical sensor 502, and physiological sounds 508 traveling through the ear canal 530 (and towards the earpiece 517) are sampled by the physiological acoustical sensor 501. Because the tympanic membrane and other body parts and tissues naturally vibrate in response to external sounds 507, part of the physiological acoustical energy 508 is composed of environmental acoustical energy 507 as well as physiological sounds. These physiological sounds are referred to as "auscultatory" information. By comparing digitized signals from each acoustical sensor 501, 502, the external energy 507 signatures can be at least partially removed from the auscultatory 508 signatures such that a new signal, containing cleaner physiological information, can be generated. For example, the sounds of external steps and human voices can be digitally removed or reduced from the final processed signal such that the final signal contains a cleaner representation of the internal sounds of pulse rate, breathing rate, swallowing rate, and other auscultatory information.

The acoustical sensors 501, 502 can contain any acoustical transducer, such as a microphone, piezoelectric crystal, vibrating membrane, magnetic recorder, and the like. Further, the acoustical sensors 501, 502 may contain a variety of layers for filtering sounds and promoting the directional extraction of sound. Additionally, various electrical filters, such as low-pass, high-pass, band-pass, notch, and other filters, can be used to clean-up signals from each sensor 501, 502 to help remove unwanted sounds or signatures. In some embodiments, the acoustical sensors 501, 502 are compact microphones, such as electric microphones or piezoelectric microphones, and the signals from these microphones are electrically filtered. The acoustical buffer region 519 can be any material that absorbs acoustical energy. In some embodiments, this material is soft, durable material, such as plastic, foam, polymer, or the like. In some embodiments, the acoustical buffer region 519 can be specially shaped to reflect or absorb sounds of certain frequencies through acoustical interference.

Figure 8:
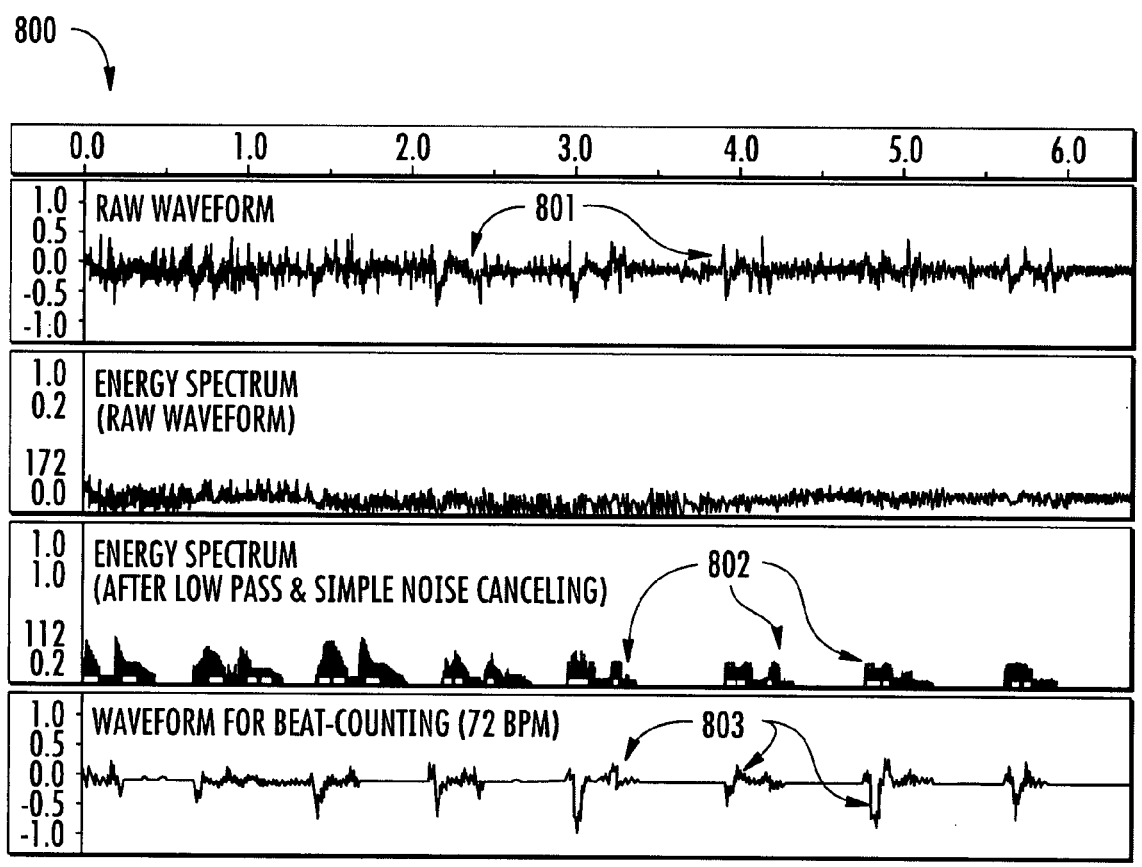
FIG. 8 illustrates experimental auscultatory data obtained via the auscultatory signal extraction approach of FIG. 5.

An example of how the auscultatory signal extraction technique 500 may be used is summarized in test data 800 set forth in FIG. 8. A small microphone was placed inside the ear of a test subject, and various sounds were recorded over time. In the test data 800, the user was relaxing on a chair. The raw waveform 801 contains information from internal and external sounds. However, following digital filtering and noise cancellation, the final energy spectrum 802 and waveform 803 contain cleaner information about the test subject's pulse rate. In fact, the signature of each pulse can even be identified. In processing this signal, the noise reduction algorithm was selected by intelligently choosing a data segment dominated by external (environmental) acoustical energy, where physiological information was largely not present. Such intelligent algorithms can be integrated into a Bluetooth earpiece module for automatic auscultatory analysis for extracting physiological sounds from the body. Because the nature of external sounds and internal sounds are known by the placement of sensors 501, 502, providing a basis for signal subtraction, the acoustical signal extraction innovation 500 can provide clean auscultatory data automatically in real-time.

Figure 6:
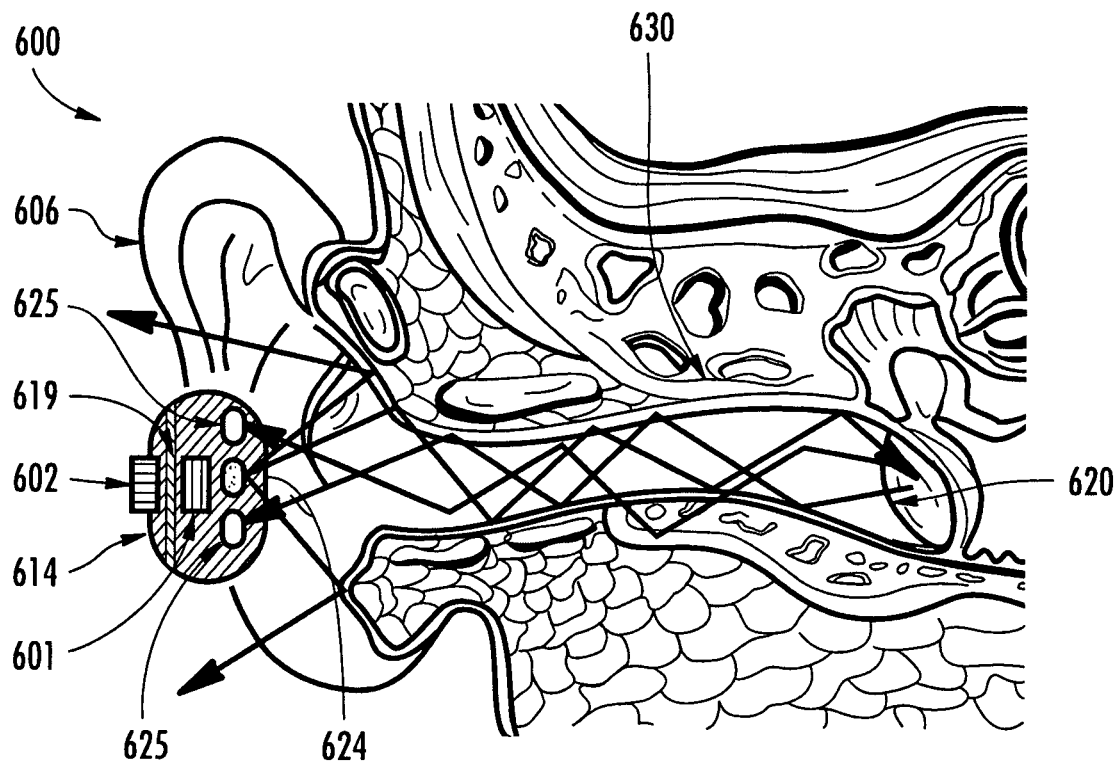
FIG. 6 illustrates an optical physiological signal extraction technique, according to some embodiments of the present invention, and wherein optical information scattered from the tympanic membrane is digitally compared with acoustical energy from the environment to generate an extracted signal containing cleaner physiological information than raw optical information scattered from the tympanic membrane.

Another embodiment of the signal extraction methodology 400 is presented in FIG. 6. The optical physiological signal extraction technique 600 is a method of extracting a variety of physiological information form the tympanic membrane 620 by locking-in to the vibrational frequency of the tympanic membrane 620. In this method 600, the earpiece module 614 contains at least one acoustical energy sensor 601 for measuring acoustical energy coming from the ear canal 630 and other neighboring organs and tissues. At least one optional external acoustical energy sensor 602 can be used for measuring environmental sounds in the vicinity of the earpiece user, as the combined signals from sensors 601, 602 can produce a cleaner signal for physiological monitoring. At least one optical emitter 624 is located in the earpiece for generating optical energy directed towards the tympanic membrane 620 through the ear canal 630. This optical energy is absorbed, scattered, and reflected by the ear canal 630 and tympanic membrane 620. In some cases, the optical energy induces fluorescence in the ear canal or tympanic membrane. In other cases, the optical energy experiences a change in polarization or other optical properties. In many cases, a change in more than one optical property (absorption, reflection, diffraction, fluorescence, polarization, etc.) occurs. In any case, this resulting optical energy is referred to as the "secondary energy." The secondary energy is detected by at least one optical detector 625, though more than one optical detector 625 may be utilized. As with the acoustical sensors 601, 602, the optical detector 625 converts incoming energy (in this case optical energy) into an electrical signal to be sent to a signal processor 405 (FIG. 4). The optical detector 625 may contain filters for selectively passing optical energy of physiological interest. A buffer region 619 is used to prevent external sound and light from convoluting the extraction of physiological information. In many cases, the optical energy generates a secondary response that is not optical in origin, such as a thermal response or biochemical response. In such case, at least one optical detector 625 may be replaced with at least one other type of sensor for sensing the non-optical secondary response.

Because the thin tympanic membrane 620 vibrates significantly in response to sound, whereas the other physiological ear features, such as the ear canal 630 and external ear 606 do not vibrate significantly, a method of extracting secondary optical signals scattered from the vibrating tympanic membrane 620 is provided. Acoustical information from the tympanic membrane vibrational response, collected by the acoustical sensor 601 (or a combination of sensors 601, 602), is processed by a signal processor 405, and the secondary optical information from the tympanic membrane is collected by the optical detector(s) 625. The signal processor compares digitized signals from these sensors in synchronized time, such that signals from the optical detector 625 containing frequency components characteristic of the tympanic membrane's vibrational response are selectively extracted to provide cleaner physiological information from the tympanic membrane. For example, the oxygen content of blood in the tympanic membrane can be monitored by the reflection of red and infrared light from the tympanic membrane, similar to pulse-oximetry. However, scattered optical energy from the ear canal may make it difficult to extract blood oxygen from the tympanic membrane, as the source of scattered light is unclear. The optical physiological signal extraction methodology 600 provides a means of locking-in to the tympanic membrane optical reflection signal through the tympanic membrane vibrational signal collected by the acoustical sensor 601 (or the combination of sensors 601, 602). The illustrated methodology 600 works because the thin tympanic membrane 620, in response to sound, vibrates with substantially greater deflection than the ear canal, and thus primary and secondary light scattered from the tympanic membrane 620 is largely modulated by the frequency of sound reaching the tympanic membrane. This same technique 600 can be applied towards monitoring scattered optical energy from the vibrating bones of the ear, using electromagnetic wavelengths capable of passing through the tympanic membrane.

Another non-limiting embodiment of the optical physiological signal extraction methodology 600 of the present invention involves dosimetry. For example, the concentration of a drug and/or the performance of a drug can be monitored over time by characterizing the real-time fluorescence response of the drug, or intentional fluophores placed in the drug, via the tympanic membrane. In such case, the fluorescence response of the tympanic membrane can be extracted from optical noise through the illustrated methodology 600. However, in this case the fluorescence response, as opposed to the reflectance response, is extracted from the tympanic membrane 620.

In the optical physiological signal extraction methodology 600, a variety of devices can be used for the optical source or optical sources 624, such as a light-emitting diode (LED), a laser diode (LD), a miniature lamp (such as a miniature incandescent lamp, a miniature mercury lamp, or a miniature tungsten lamp), a light guide delivering light from an outside source (such as the sun or other light source), a multi-wavelength source, a microplasma source, an arc source, a combination of these sources, and the like. Special variants of light-emitting diodes, such as resonant-cavity light emitting diodes (RCLEDs), superluminescent LEDs (SLEDs), organic LEDs (OLEDs), and the like can also be applied.

In some embodiments of FIG. 6, coherent light can be used to monitor physiological processes. Monitoring vibrating membranes can be accomplished by using lasers and LDs such that coherent optical energy can directly interrogate the membrane and interference signals can be extracted. However, the signal extraction approach of FIG. 6 allows physiological signal extraction from the tympanic membrane with incoherent light-emitting diodes, which use less power, are more commercially available, and are more cost-effective than laser diodes. In fact, the scattered light from LEDs can be an advantage as scattered light may be necessary for reaching the tympanic membrane from outside of the ear canal. More specifically, earpiece module users may prefer to not have a tube stuck deep into the ear canal, and thus there may be no direct, unobstructed optical path to the tympanic membrane from outside of the ear.

It should be noted that in some cases the optical physiological signal extraction methodology 600 can be implemented without the optical emitter 624. For example, the native IR blackbody radiation of the tympanic membrane, scattered in proportion to acoustical vibrational motion of the tympanic membrane, can be extracted using the approach 600 of FIG. 6 without the need of an optical emitter 624. This may be accomplished by locking-in to the acoustically modulated blackbody IR radiation from the tympanic membrane, sensed by the photodetector 625, through the signals received by the acoustic sensor 601 or 602. The extracted blackbody radiation from the tympanic membrane can then be processed by a signal processor 103 to yield a resulting signal indicative of core body temperature. In this embodiment, the photodetector 625 may be, for example, an IR sensor, an IR photodiode, an IR avalanche photodiode, an IR photoconductor, an IRdetecting field-effect transistor, a fast-response thermal sensor such as a pyroelectric sensor, or the like.

Figure 7:
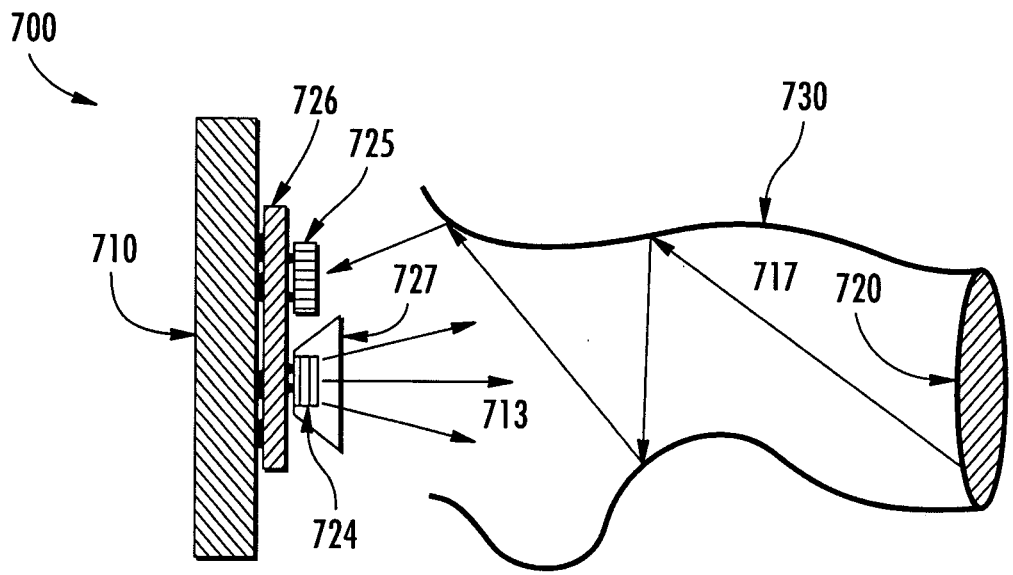
FIG. 7 illustrates an optical source detector configuration, according to some embodiments of the present invention, for the physiological signal extraction method illustrated in FIG. 6.

A specific pictorial example of the innovative optical physiological signal extraction methodology 600, incorporating an LED-photodetector module 700, is shown in FIG. 7. In the illustrated module 700, at least one LED 724 generates at least one optical beam 713 directed towards the tympanic membrane 720 through the ear canal 730. At least one photodetector 725 is positioned to receive scattered light 717 modulated by the tympanic membrane 720. Inevitably, scattered light from the ear canal 730 not associated with the tympanic membrane will also reach the photodetector 725. The optical physiological signal extraction methodology 600, according to some embodiments of the present invention, can be used to reduce the impact of scattered light from the ear canal 730 and increase the impact of scattered light from the tympanic membrane 720.

An optical reflector 727 may be used to steer the light from the LED 724 towards the tympanic membrane 720 and away from the photodetector 725, preventing convolution and saturation by the optical source light 713. The LED 724 and photodetector 725 are mounted onto a mounting board 726 in a discrete module, and this discrete module may be mounted to a larger board 710 for integration with circuitry in an earpiece sensor module 100. Mounting of components to the board 726 and the board 726 to the larger board 710 can be accomplished, for example, by heating soldering bumps underneath the parts through standard electronic soldering techniques. The photodetector 724 can be any solid state device, such as a photodiode, an avalanche photodiode, a photoconductor, a photovoltaic, a photomultiplier, a FET photodetector, a photomultiplier tube, or the like. In some cases, the larger mounting board 710 may be connected to a detachable element, such as a cable, jack, fixture, or the like.

The active optical absorption region of the photodetector 725 may be covered by at least one optical filter for selectively passing light of interest. Light-guiding optics may also be integrated. Optical filters and light-guiding optics may also be applied to the LED source 724. The LED 724 can be any optical wavelength from the deep-UV to the deep-IR. In some cases, the LED 724 can be replaced with a laser diode or other compact laser source, as long as electrical powering requirements are satisfied. In such case, the laser diode may need to be pulsed on a set interval to prevent a battery drain from continuous laser diode usage.

Referring back to FIG. 4, the directional external energy sensors 402, 403, and 404 can be useful for monitoring multiple sounds at once and deconvoluting interference from other sounds. For example, to monitor footsteps (pedometry), physical activity, and/or the impact on vital signs, signals from the sensors 401, 402, 403, and 404 can all be processed together, via the signal processor 405, to generate meaningful information about each factor. More specifically, the sound of footsteps can be extracted from the final processed signal by deconvoluting directional sounds from above the earpiece user, through Sensor-3 403, and by deconvoluting directional sounds from the side of the earpiece user, through Sensor-2 402. In this manner, sounds from footsteps, coming primarily from below the user, measured through Sensor-4 404, and from inside the user, measured through Sensor-1 401, can be extracted from interfering sounds coming from other, non-relevant directions.

According to some embodiments of the present invention, a person's vitals signs can be extracted through the same methodology, but in this case, the sounds measured from at least one external energy sensor (Sensor-2, Sensor-3, or Sensor-4 404) are also deconvoluted from the final signal such that the final signal contains cleaner physiological information than that from Sensor-1 401 alone. As a further example of the acoustical signal extraction methodology 500 of the present invention, the signal extraction technique can be used to extract acoustical signals associated with one or more of the following: yawning, swallowing, eating, masticating, sleeping, slurping, walking, running, physical activity, jogging, jumping, teeth grinding, jaw movements, a change in bite, changes in speech, changes in voice (volume, pitch, speed, inflammation of vocal chords, etc.), coughing, snoring, sneezing, laughing, eye muscle movements, crying, yelling, vocal stress, physical and psychological stress, stuttering, digestion, organ functioning, vital signs, pulse rate, breathing rate, cardiovascular performance, pulmonary performance, lung capacity, breathing volume, blood pressure, athletic performance, physiological or psychological stress indicators, the number of typed words on a keyboard or typing rate, personal habits (such as scratching, nail biting, saying "um," hair pulling, smoking, and the like), emotional states, muscle tension, and the like.

It should be clear that the general physiological signal extraction methodology 500 is also applicable in the reverse. Namely, the external environmental energy can be extracted from the convolution of external energy with physiological energy through the same basic process. In such case, the signal processor 405 subtracts signatures associated with internal physiological energy such that the new processed signal contains cleaner information about the environment. It should also be clear that any of the sensors 401, 402, 403, and 404 can be composed of multiple sensors measuring multiple forms and expressions of various physical energies.

The earpiece modules described herein need not be embodied within headsets. For example, an earpiece module 100 according to embodiments of the present invention can be a hearing aid, an earplug, an entertaining speaker, the earpiece for an IPOD, Walkman, or other entertainment unit, a commercial headset for a phone operator, an earring, a gaming interface, or the like. The earpiece module 100 covers the broad realm of earpieces, ear jewelry, and ear apparatuses used by persons for entertainment, hearing, or other purposes both inside and outside of health and environmental monitoring.

Moreover, two earpiece modules 100 may be utilized, one for each ear of a person, according to some embodiments of the present invention. Dual-ear analysis with two earpiece modules can be used, for example, to compare the core temperature of each tympanic membrane in order to gauge brain activity comparing each brain hemisphere. In another case, acoustical energy, including ultrasonic energy, can be passed from one earpiece module to the other, with acoustic absorption and reflection being used to gauge various physiological states. For example, this technique can be used to gauge hydration level in the head or brain by estimating the acoustical energy absorption rate and sound velocity through the head of the user.

A variety of earpiece styles, shapes, and architectures can be used for earpiece module 100 according to embodiments of the present invention. A non-limiting embodiment of the earpiece module is shown pictorially in FIG. 9. The illustrated earpiece 905 fits over the ear of a person and is held in place by an ear support 901 (also called the "earpiece attachment component" 105). The illustrated earpiece module 905 also includes an earpiece body 902, an earpiece fitting 908, and an optional earlobe clip 904. The earpiece may also contain an adjustable mouthpiece 1416 (FIG. 14B) and/or a pinna cover 1402 (FIGS. 14A-14B) described below. The earpiece 905 connects with the ear canal of a person through an earpiece fitting 908 located on the backside 906 of the earpiece 905. The earpiece fitting 908 transmits sound to the inner ear and eardrum. Health and environmental sensors are integrated primarily within or along the earpiece body 902, including the earpiece backside 906. However, an earlobe clip 904 can contain various health and environmental sensors as well. In some cases, health and environmental sensors can be integrated within or along the ear support 901, the adjustable mouthpiece 1416, the earpiece fitting 908, or the pinna cover 1402. Raw or processed data 903 from these sensors can be wirelessly transferred to a recording device or a portable telecommunication device 210 (FIG. 2). In some embodiments of the present invention, a recording device can be located within or about the earpiece 905 itself. In some cases, this recording device is flash memory or other digitized memory storage. The types of health and environmental factors which may be monitored have been previously described above for the earpiece module 100.

It should be understood that the earpiece body 902 can be any shape and size suitable for supporting an earpiece fitting 1008. In some cases, the earpiece body and earpiece fitting can be one and the same structure, such that the earpiece body-fitting is a small fitting inside the ear. In many cases, it is desirable to seal off or partially seal off the ear canal so as to prevent sounds from entering or leaving the ear such that auscultatory signal can more easily be extracted from the ear canal through devices (such as microphones) in the earpiece body-fitting.

Figure 9:
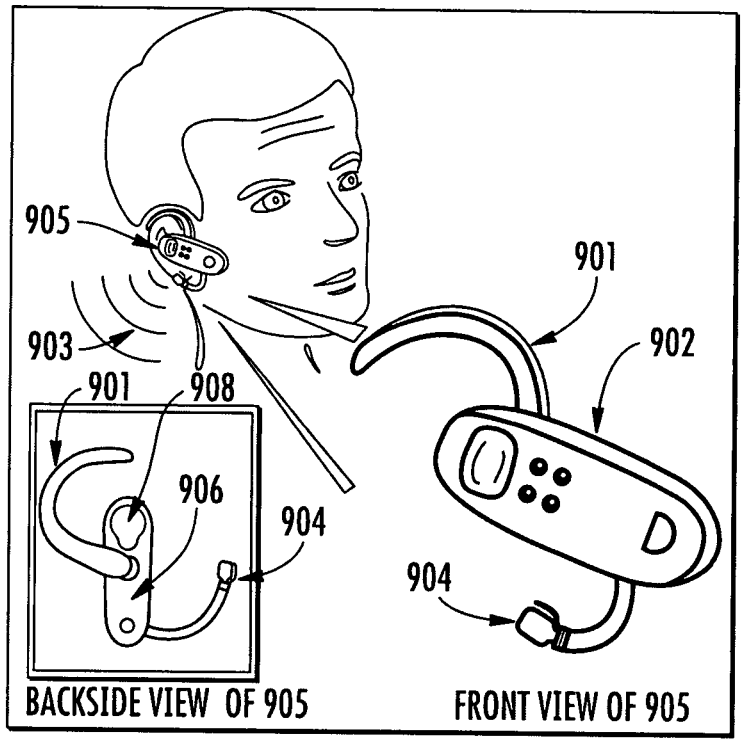
FIG. 9 illustrates an earpiece module according to some embodiments of the present invention.
Figure 12:
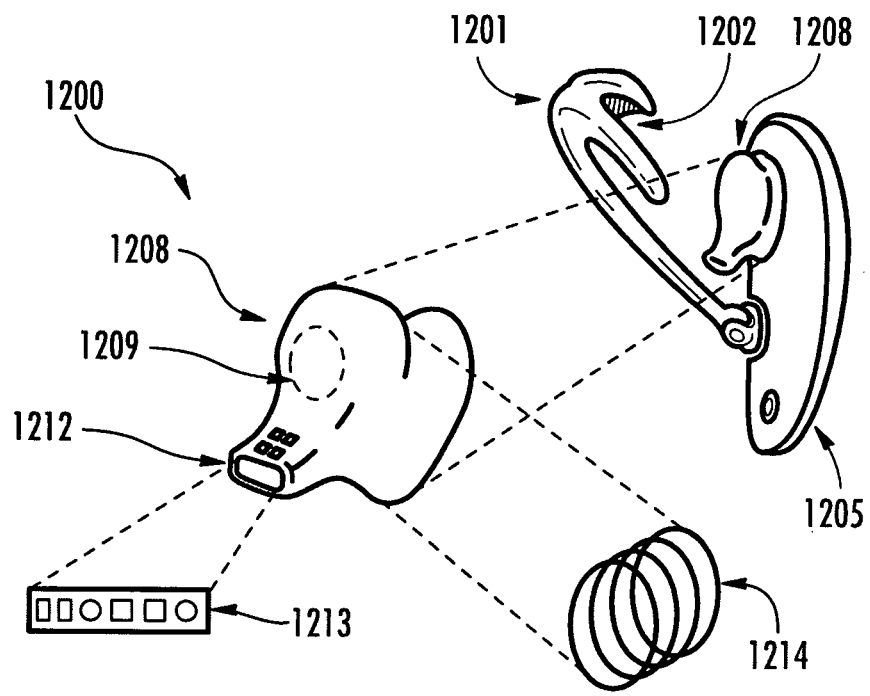
FIG. 12 is an exploded view of the earpiece module of FIG. 9 showing a location of various physiological sensors, according to some embodiments of the present invention.

It should be noted that the invention is not limited to the exemplary earpiece 905 of FIG. 9. Other earpiece configurations are also capable of integrating health and environmental sensors for portable, noninvasive, real-time health monitoring according to embodiments of the present invention. For example, the earlobe clip 904 can be modified to reach other surfaces along or near a person's ear, head, neck, or face to accommodate electrical or optical sensing. Similarly, more than one clip may be integrated into the earpiece 905. Sensors can be integrated into the earpiece-fitting 1008 as shown in the earpiece 1002 of FIG. 10. In such embodiments, the sensors may be integrated into a module 1009 in the earpiece-fitting 1008. Environmental sensors are preferably located on the outside of the earpiece 1205 through a region on the earpiece frontside 1206 (as shown in FIG. 12). This allows access to air in the vicinity of the earpiece user. However, environmental sensors can be located anywhere along the earpiece module 905.

FIG. 12 illustrates details about the location of sensors in certain parts of an earpiece module 1205, according to embodiments of the present invention. The ear support 1201 contains a pinna cover 1202 that may contain sensors for monitoring physiological and environmental factors. This structure is particularly useful for sensing methodologies which require energy to be transmitted through the thin layers of the pinna (the outer ear). Though any portion of the pinna can be covered and/or contacted, in some embodiments, the pinna cover 1202 overlaps at least a part of the helix or a part of the scapha of an ear. Likewise, an optical absorption detector, composed of an optical emitter and optical detector, can be integrated into the pinna cover 1202 for monitoring, for example, hydration, dosimetry, skin temperature, inductive galvanometry, conductive galvanometry, and the like.

Galvanometry, the measurement of electrical properties of the skin, can be measured inductively, through contactless electromagnetic induction without contacts, or conductively, with two, three, four, or more conductivity probes. Additionally, a 4-point conductivity probe technique, such as that used for measuring the conductivity of semiconductor wafers, can be applied. A variety of sensors can be integrated into the earpiece fitting 1208. For example, a galvanometric device can be integrated into the surface 1209 of the earpiece fitting where the earpiece fitting touches the skin of the outer ear. Additionally, an inductive device, such as an inductive coil 1214, can be integrated along the earpiece fitting body to measure movements of the tympanic membrane inductively. The inductive impedance can also be measured with the inductive coil 1214 or another inductive sensor, and this can be applied towards contactless galvanometry. The inductive coil 1214 can include one or more coils arranged in any orientation, and a core material, such as an iron-containing material, may be used to improve the sensitivity of the response. In some cases, multiple coils may be used to facilitate the canceling of stray electromagnetic interference. Sensors can also be integrated into the end tip 1212 of the earpiece fitting 1208 to measure physiological properties deeper into the ear canal. For example, the optical module 700 of FIG. 7 may be located in, at, or near the end tip region 1212 in a module 1213. The sensors on the module 1213 in this region are carefully arranged so as not to prevent the transmission of sound (from the built-in communication module 107) and to not be distorted during earpiece placement and removal. The end tip sensor module 1213 can contain several types of sensors for generating multiple types of energy and detecting multiple types of energy, and this module can be integrated into the speaker module (part of the communication module 107) inside the earpiece fitting 1208 that is used for sound transmission to the user during telemetric conversations. In some cases, the speaker module can be used as a microphone to measure auscultatory signals from the body. This may be especially useful for measuring low frequency signals less than 1000 Hz. Employing the speaker as a microphone may require impedance matching to maximize the auscultatory signal extraction.

Figure 13:
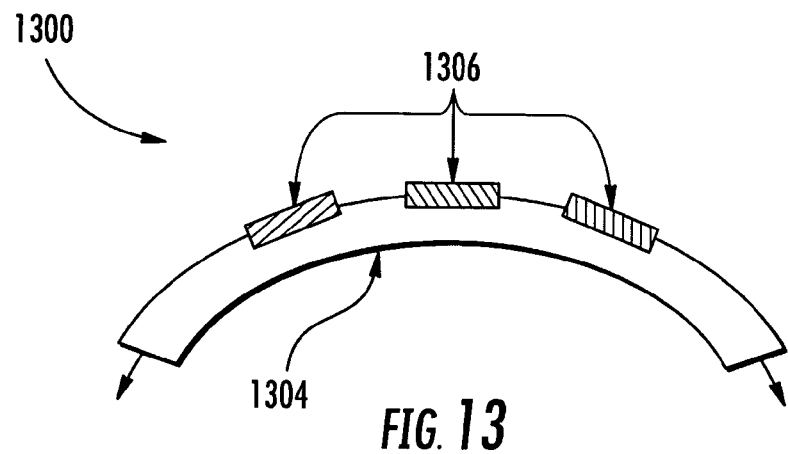
FIG. 13 is a side view of a flexible substrate configured to place sensors in selected locations in the vicinity of the ear, according to some embodiments of the present invention.

Alignment, placement, and arrangement of sensors, according to embodiments of the present invention, can be enabled or simplified by adopting a flexible circuitry configuration 1300, such as that shown in FIG. 13. A flexible circuit board 1304 according to embodiments of the present invention can be made out of any stable flexible material, such as kapton, polymers, flexible ceramics, flexible glasses, rubber, and the like. A key requirement of the flexible material of the flexible circuit board 1304 is that it must be sufficiently electrically insulating and electrochemically inert. As with a standard rigid circuit board, a variety of sensors 1306 can be mounted on the flexible circuit board 1304, and this board can be integrated into any part of the earpiece module 905 (FIG. 9). Flexible circuitry can be especially useful for odd-shaped components of the earpiece, such as the earpiece fitting 908, ear support 901, the earpiece clip 904, the adjustable mouthpiece 1416, and the pinna cover 1202/1402. In some cases, flexible piezoelectric polymers, such as polyvinylidene fluoride may be useful for measuring body motion and auscultatory sounds from the body.

Figures 14A, 14B:
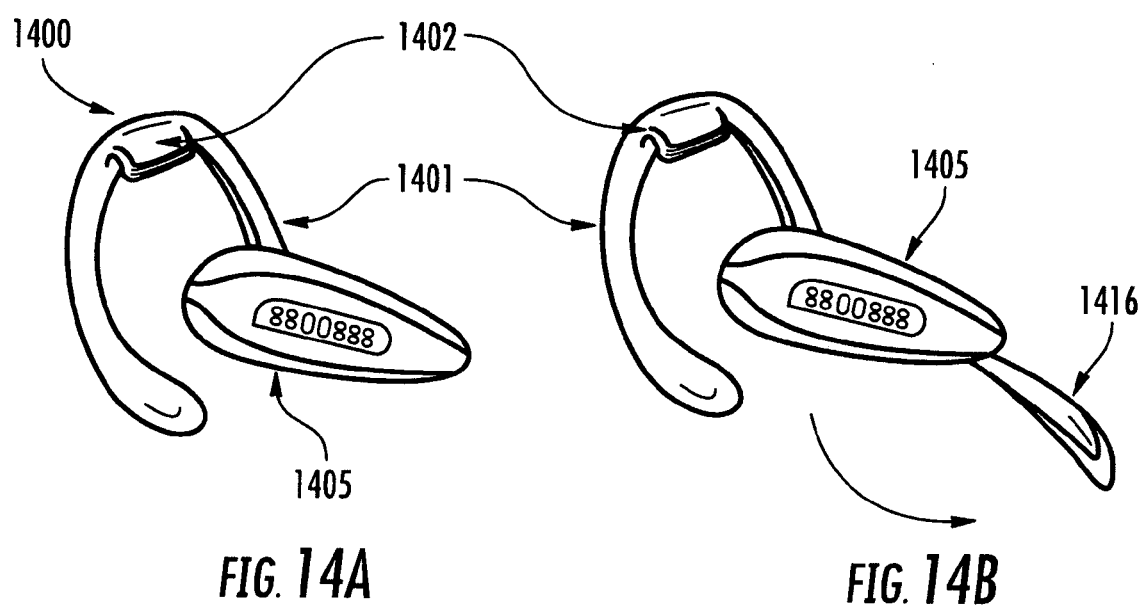

FIGS. 14A-14B illustrate an embodiment 1400 of an earpiece module 1405 with an adjustable mouthpiece 1416 and a pinna cover 1402. The earpiece 1400 contains a region where an adjustable mouthpiece 1416 can be swiveled, extended, pulled, extracted, flipped, or ejected towards the mouth. A microphone at the end of the mouthpiece 1416 can be used to improve personal communication through the earpiece 1400. Sensors integrated into the mouthpiece 1416 can be used to monitor, for example, exhaled breath for respirometry and inhalation/exhalation monitoring. Carbon dioxide, oxygen, nitrogen, water vapor, and other respired gases and vapors can be monitored, providing an overall assessment of health.

Additionally, VOC's and other vapors exhaled by the breath can be monitored for diagnosing various disease states, such as diabetes, obesity, diet, metabolism, cancer, hepatic or renal health, organ functioning, alcoholism, halitosis, drug addiction, lung inflammation, voice analysis, voice distinction, and the like. The mouthpiece 1416 is in a retracted or stored position in FIG. 14A and is in an extended or operative position in FIG. 14B.

Figure 15:
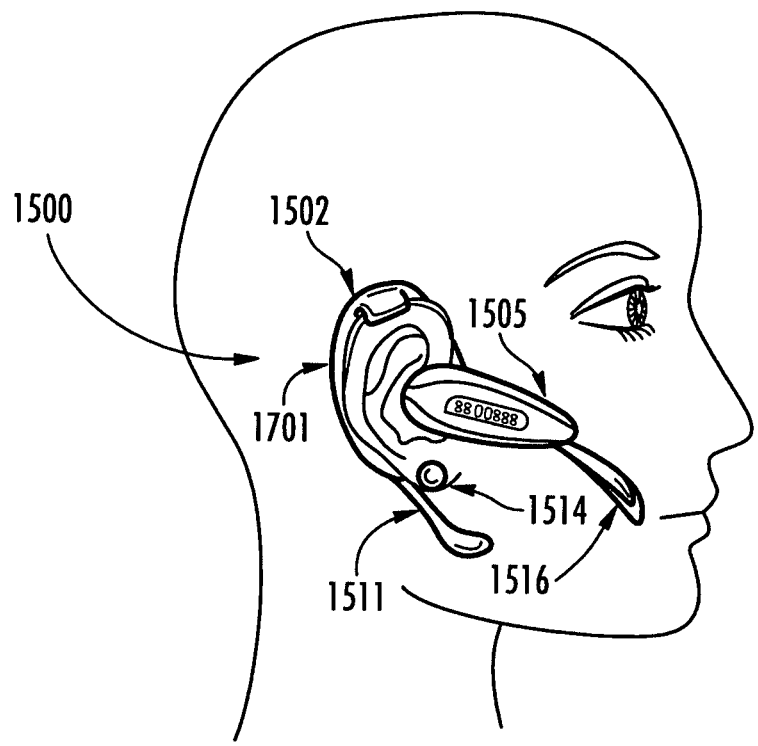
FIG. 15 illustrates an earpiece module incorporating various physiological and environmental sensors, according to some embodiments of the present invention, and being worn by a user.

Another multifunctional earpiece module 1500, according to embodiments of the present invention, is illustrated in FIG. 15. The illustrated earpiece module 1500 includes the embodiments described with respect to FIGS. 9 and 14A-14B, such as a pinna cover 1502, an ear support 1501, a mouthpiece 1516, an earpiece body 1505, and the like. Additionally, the earpiece module 1500 may contain an extension 1511 with sensors for monitoring jaw motion, arterial blood flow near the neck, or other physiological and environmental factors near the jaw and neck region.

The person illustrated in FIG. 15 is also wearing an earring monitor 1514 according to embodiments of the present invention. Because at least one portion of an earring may penetrate the skin, earring monitor 1514 may contain sensors and telemetric circuitry that provide access to various blood analytes through iontophoresis and electrochemical sensing that may not be easily accessible by the other portions of the earpiece module 1500. Additionally, the earring may provide a good electrical contact for ECG or skin conductivity.

Figure 16:
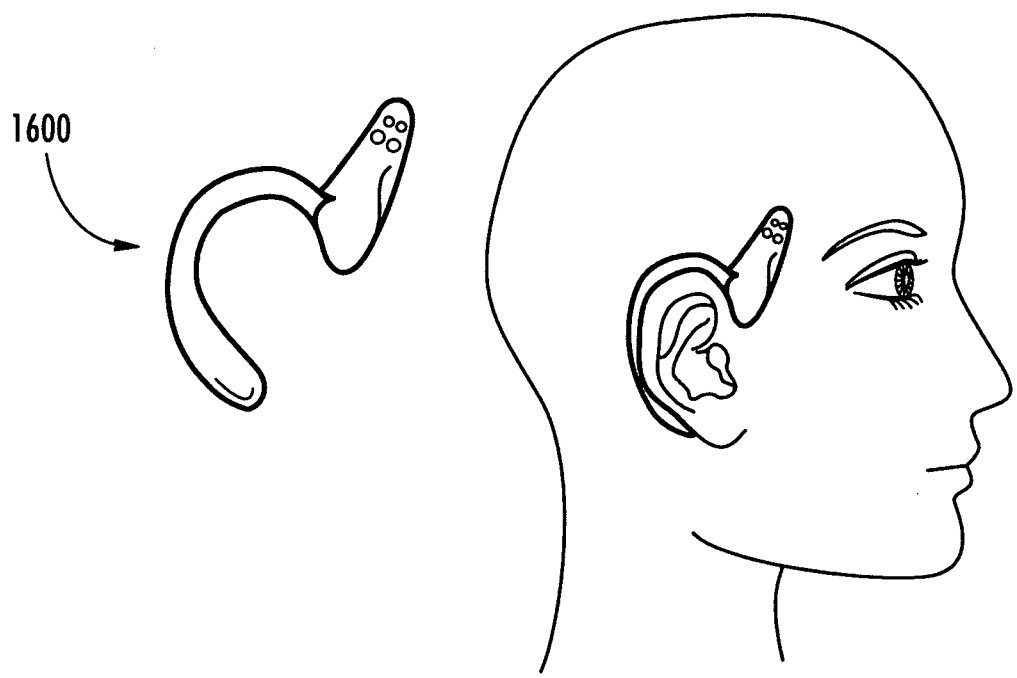
FIG. 16 illustrates an earpiece module according to other embodiments of the present invention that includes a temple module for physiological and environmental monitoring.

Embodiments of the present invention are not limited to earpiece modules. Other types of modules may be utilized that attach to other portions of a person's body. For example, a temple module 1600 having a similar design as the earpiece module design 100 can also be employed, as illustrated in FIG. 16. A temple module 1600 has the benefit of being close to physiological areas associated with stress, intracranial pressure, brain activity, and migraines. Additionally, a temple module can monitor physiological activity associated with the onset of a stroke, such as increased or decreased blood flow and/or oxygen flow to the brain.

Figure 19:
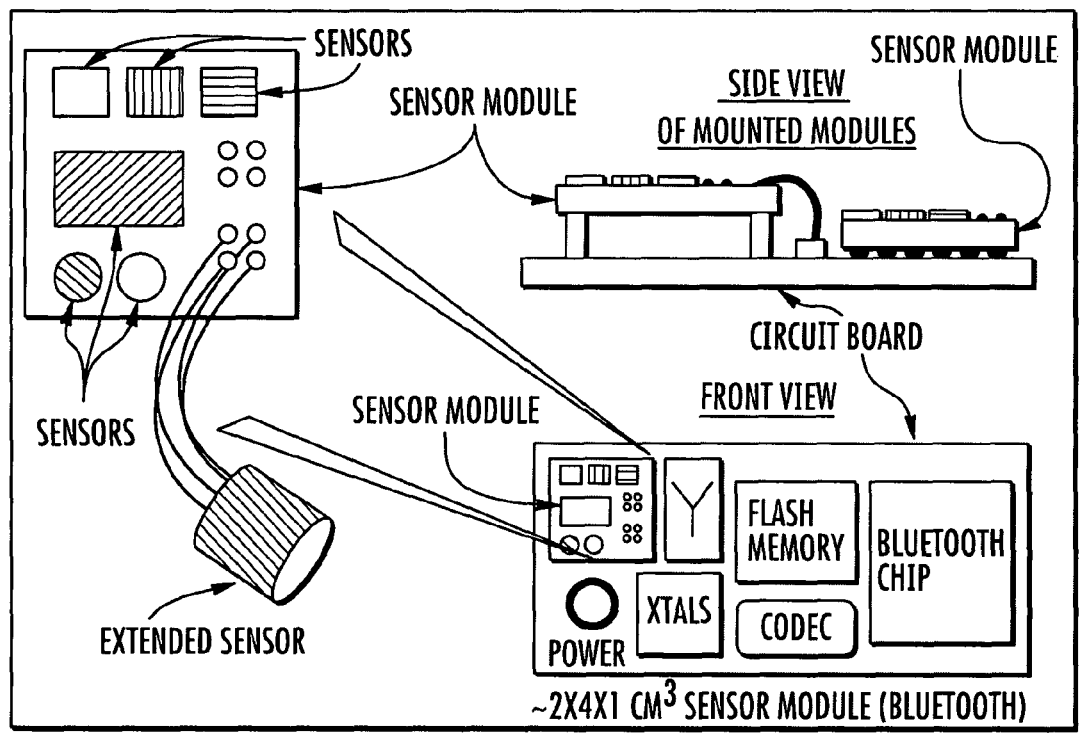
FIG. 19 illustrates a sensor module having a plurality of health and environmental sensors and mounted onto a Bluetooth headset module, according to some embodiments of the present invention.

FIG. 19 illustrates a sensor module, according to embodiments of the present invention, integrated into a telemetric Bluetooth module. Though a Bluetooth module is used in this example, it should be understood that other telemetric modules can be used. Telemetric modules according to some embodiments of the present invention may operate in open architecture protocols, allowing multiple telemetric devices to communicate with each other. A Bluetooth module (including the sensor module) according to some embodiments of the present invention is integrated into a wearable earpiece module (i.e., module 100 described above). The sensor module illustrated in FIG. 19 contains one or more sensors, and is mounted onto a Bluetooth module. In one embodiment, the sensor module is directly soldered onto the Bluetooth module. In another embodiment, the sensor module is elevated from the Bluetooth module with spacers, and a cable or electrical wires connect between the sensor module and the Bluetooth module. The module may be elevated in embodiments where the sensors need to be exposed to the environment. For example, the sensors may need to be exposed through the frontside region 1106 of an earpiece module 1105 (FIG. 11), and the Bluetooth module may fit too deeply into the earpiece module to provide sensor access to the external environment. In some cases, contact leads or vias may connect between the sensor module and an extended sensor or an additional sensor module. This allows the extended sensor or sensor module to be flexibly mounted anywhere inside, along, outside, or about the earpiece module 100. Extended sensors can be especially useful for 4-point galvanometric monitoring of skin conductance, pulse oximetry, and volatile organic compound monitoring.

Figure 20:
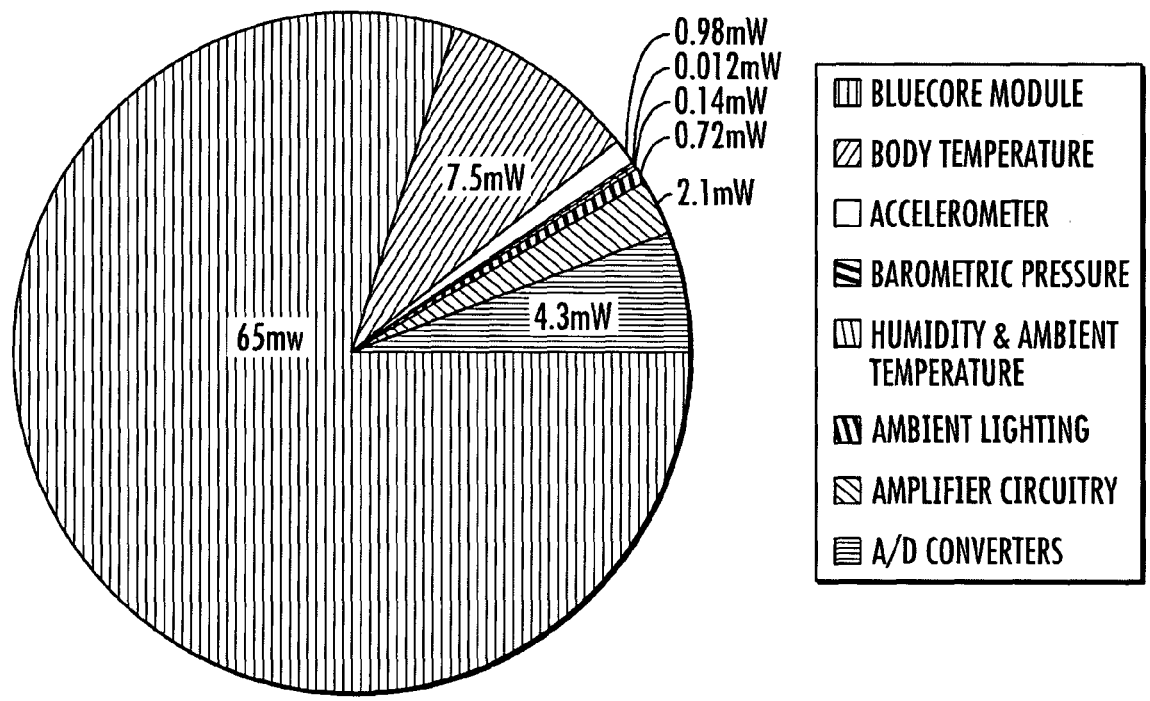
FIG. 20 is a pie chart that graphically illustrates exemplary power usage of an earpiece module for monitoring health and environmental exposure, according to some embodiments of the present invention.

FIG. 20 illustrates the power budget of a personal health and environmental monitor earpiece module, such as earpiece module 100, incorporated into a Bluecore Bluetooth module, according to some embodiments of the present invention. As illustrated, the sensor components (i.e., a body temperature sensor, 2-axis accelerometer, barometric pressure sensor, humidity sensor, ambient temperature sensor, and ambient lighting sensor) account for less than 16 mW of the total operating power of the Bluetooth-enabled earpiece module. The Bluecore Bluetooth operating power during transmission is approximately 65 mW. Combined together, the earpiece module, with all operating components, can operate with less than 100 mW of total operating power and provide a full day of sensing between recharges of typical batteries. Sensors other than these particular sensors, can also be included with minimal increase in operating power with respect to the Bluecore Bluetooth module. Pulsed sensing or "polling" of the sensors to read out data at certain intervals can further extend battery life.

Figure 17:
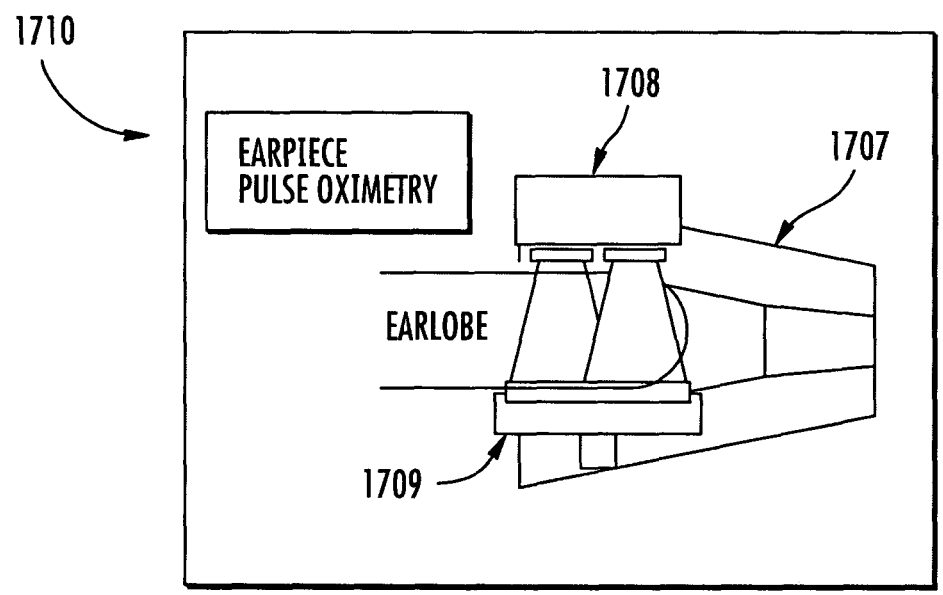
FIG. 17 illustrates a pulse-oximeter configured to be attached to an ear of a user and that may be incorporated into an earpiece module, according to some embodiments of the present invention. The illustrated pulse-oximeter is in transmission mode.

Pulse oximetry is a standard noninvasive technique of estimating blood gas levels. Pulse oximeters typically employ 2 or more optical wavelengths to estimate the ratio of oxygenated to deoxygenated blood. Similarly, various types of hemoglobin, such as methemoglobin and carboxyhemoglobin can be differentiated by measuring and comparing the optical absorption at key red and near-infrared wavelengths. FIG. 17 shows a transmittance pulse oximeter 1710 incorporated into an earpiece module (such as earpiece module 905 of FIG. 9) with the head 1707 of the earlobe clip containing an optical source 1708 and an optical detector 1709. In general, the optical wavelengths from optical source 1708 pass through arteries or veins and are selectively absorbed by various blood metabolites, typically blood gas carriers such as hemoglobin. These metabolites can change color in response to the incorporation or removal of various blood gases, such as oxygen, carbon dioxide, carbon monoxide, and other inhaled gases. The optical detector 1709 may contain optical filters to selectively detect light at key wavelengths relating to the presence or absence of the aforementioned optical absorption bands.

Though only two optical wavelengths are shown emanating from the source 1708, several additional wavelengths can be incorporated and/or replace conventional wavelengths. For example, by adding additional visible and infrared wavelengths, myoglobin, methemoglobin, carboxyhemoglobin, bilirubin, SpCO2, and blood urea nitrogen (BUN) can be estimated and/or monitored in real-time in addition to the conventional pulse oximetry SpO2 measurement.

The optical source 1708 can include light-emitting diodes (LEDs), laser diodes (LDs), or other compact optical sources. In some cases, optical energies from the optical sources can be guided with waveguides, such as fiber optics. In some cases, ambient light, such as room light or solar radiation, may be sufficient for the optical source 1708. In such case, waveguides may be used to couple ambient light towards the earlobe or other point of interest, Ambient light may be useful in that ambient light may represent a diffuse optical source that is largely independent of body position, such that motion artifacts associated with body motion may be lessened. The optical detectors 1709 can include photodiodes (PDs), avalanche photodiodes (APDs), photomultipliers, or other compact optical detectors.

Figure 18:
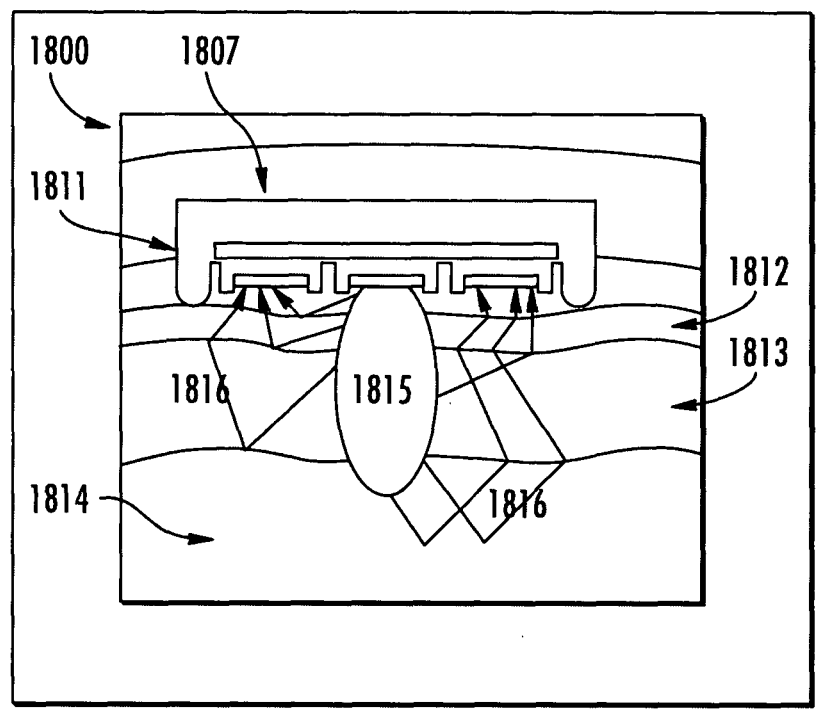
FIG. 18 illustrates a pulse-oximeter configured to be integrated into an earpiece module, according to some embodiments of the present invention. The illustrated pulse-oximeter is in reflection mode.

FIG. 18 shows a reflective pulse oximetry setup 1800 where reflected wavelengths 1816 are measured, as opposed to measuring transmitted wavelengths. In the illustrated embodiment, an optical source-detector assembly 1811 is integrated into an earlobe clip head 1807 to generate optical wavelengths 1815 and monitor the resulting reflected optical energy 1816. The optical source-detector assembly 1811 contains one or more optical sources emitting one or more optical wavelengths, as well as one or more optical detectors detecting one or more optical wavelengths. The epidermis 1812, dermis 1813, and subcutaneous 1814 layers of skin tissue are shown in FIG. 18 for reference.

The reflective pulse oximetry setup 1817 is also suitable for measuring fluorescence from various skin or blood analytes. For example, the optical sources and/or photodetectors may be selectively filtered to measure key fluorescence bands. A fluorescence approach can be applied to, for example, the real-time monitoring of cholesterol and lipids in the skin or blood. Though the optical techniques of FIG. 17 and FIG. 18 are shown primarily over the earlobe or skin, these techniques can be integrated with the optical physiological signal extraction technique 600, described above with respect to FIG. 6, for measuring blood gas properties at or near the tympanic membrane.

Blood hydration can also be monitored optically, as water selectively absorbs optical wavelengths in the mid-IR and blue-UV ranges, whereas water can be more transparent to the blue-green wavelengths. Thus, the same optical emitter/detector configuration used in earpiece pulse oximetry (FIGS. 17 and 18) can be employed for hydration monitoring. However, mid-IR or blue optical emitters and detectors may be required. Additionally, monitoring the ratio of blue-green to other transmitted or reflected wavelengths may aid the real-time assessment of blood hydration levels. Blood hydration can also be monitored by measuring changes in capacitance, resistance, or inductance along the ear in response to varying water content in the skin tissues or blood. Similarly, hydration can be estimated by monitoring ions extracted via iontophoresis across the skin. Additionally, measuring the return velocity of reflected sound (including ultrasound) entering the head can be used to gauge hydration. These hydration sensors can be mounted anywhere within or along an earpiece. For example, with respect to the earpiece 905 of FIG. 9, hydration sensors can be mounted to a body 902 of the earpiece, the ear support 901, the earpiece backside 906, an earlobe clip, a pinna cover 1402, an earpiece fitting 1208, and the like. For monitoring hydration properties through the tympanic membrane, the earpiece tip 1212 of the earpiece fitting 1208 may be ideal for a sensor module (such as 1213). It should be noted that other hydration sensors can also be incorporated into a module.

A variety of techniques can be used for monitoring blood metabolites via an earpiece module, such as earpiece module 100. For example, glucose can be monitored via iontophoresis at the surface of the skin combined with enzyme detection. Blood urea nitrogen (BUN) can be monitored by monitoring UV fluorescence in blood (through the skin) or by monitoring visible and mid-IR light absorption using the pulse oximetry approach described above. Various ions such as sodium, potassium, magnesium, calcium, iron, copper, nickel, and other metal ions, can be monitored via selective electrodes in an earpiece module following iontophoresis through the skin. The optical physiological signal extraction approach 600 described above can be used to monitor glucose from the tympanic membrane by monitoring optical reflection and optical fluorescence from the tympanic membrane in response to IR and blue light.

Cardiopulmonary functioning can be evaluated by monitoring blood pressure, pulse, cardiac output, and blood gas levels via earpiece modules, and other monitoring apparatus in accordance with some embodiments of the present invention. Pulse rate and intensity can be monitored through pulse oximetry (described above) as well as by sensing an increase in oxygenated blood with time. Pulse rate and blood flow may also be assessed through impedance measurements via galvanometry near a blood vessel. Additionally, pulse rate and blood flow may be assessed through a fast-response thermal energy sensor, such as a pyroelectric sensor. Because moving blood may temporarily increase or decrease the localized temperature near a blood vessel, a pyroelectric sensor will generate an electrical signal that is proportional to the total blood flow in time. Blood pressure can be monitored along the earlobe, for example. According to some embodiments of the present invention, a digital blood pressure meter is integrated into an earpiece module, such as earpiece 905 of FIG. 9. A compact clip, similar to 1707 of FIG. 17, containing actuators and sonic and pressure transducers, can be placed along the earlobe, and systolic and diastolic pressure can be measured by monitoring the pressure at which the well-known Korotkoff sound is first heard (systolic), then disappears (diastolic). This technique can also be used to monitor intra-cranial pressure and other internal pressures. Blood pressure may also be measured by comparing the time between pulses at different regions of the body. For example, sensors for monitoring pulse rate and blood volume can be located in front of the ear and behind the ear or at the earlobe, and the time between the detection of each pulse from each sensor, as well as the volume of blood passed, can be processed by the signal processor 103 into an indication of blood pressure. Electrodes within or about an earpiece can also be utilized to monitor blood gases diffused through the skin, giving an indication of blood gas metabolism. For example, a compact Severinghaus electrode can be incorporated within an earpiece module for the real-time monitoring of $CO_2$ levels in the blood, for example, through an earlobe connector, a sensor region of an earpiece fitting, or along or about an ear support. These Severinghaus-type electrodes can also be used to monitor other blood gases besides $CO_2$, such as oxygen and nitrogen.

Organ function monitoring includes monitoring, for example, the liver, kidneys, pancreas, skin, and other vital or important organs. Liver quality can be monitored noninvasively by monitoring optical absorption and reflection at various optical wavelengths. For example, optical reflection from white LEDs or selected visible-wavelength LEDs can be used to monitor bilirubin levels in the skin and blood, for a real-time assessment of liver health.

Monitoring neurological functioning can be accomplished via electrodes placed at the ear, near the ear, or along another surface of the body. When such electrodes are placed along the forehead, this process is described as electroencephalography, and the resulting data is called an electroencephalogram (EEG). These electrodes can be either integrated into an earpiece module or connected to an earpiece module, according to some embodiments of the present invention. For example, an earlobe clip (e.g., 904, FIG. 9) can be modified to conform with EEG electrodes or other electrodes for measuring brain waves or neurological activity. For monitoring neurological functioning, a temple earpiece (e.g., 1600, FIG. 16) may also be used. Electrodes may be positioned in a temple earpiece region near the temples of a user for direct contact with the skin. In some embodiments, direct contact is not necessary, and the neurological functioning can be monitored capacitively, inductively, electromagnetically, or a combination of these approaches. In some embodiments, brain waves may couple with low frequency acoustical sensors integrated into an earpiece module.

A person's body motion and head position can be monitored by integrating a motion sensor into an earpiece module (e.g., 905, FIG. 9) Two such compact motion sensors include gyroscopes and accelerometers, typically mechanical or optical in origin. In some embodiments, an accelerometer may be composed of one or more microelectromechanical systems (MEMS) devices. In some embodiments, an accelerometer can measure acceleration or position in 2 or more axes. When the head is moved, a motion sensor detects the displaced motion from the origin. A head position monitor can be used to sense convulsions or seizures and relay this information wirelessly to a recording device. Similarly, head position monitoring may serve as a feedback mechanism for exercise and athletic training were head positioning with respect to the body is important. Additionally, the head position monitoring can be used to monitor when someone has fallen down or is not moving.

Figure 10:
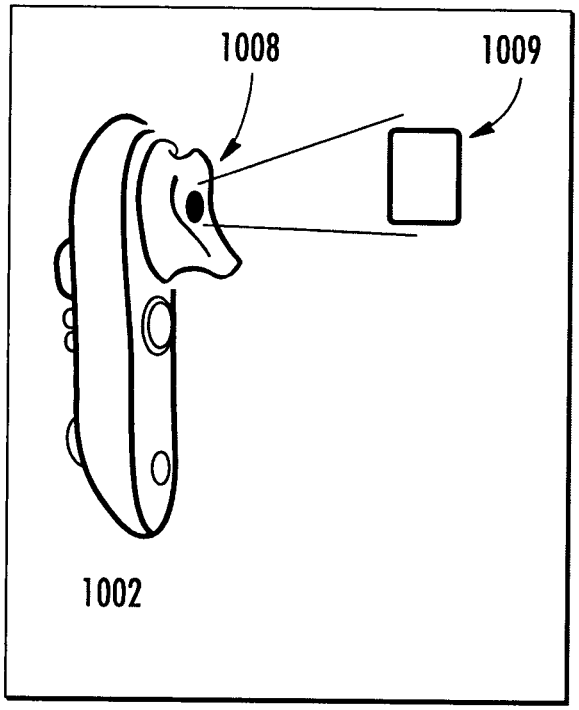
FIG. 10 is a side view of the earpiece module of FIG. 9 showing a placement of physiological sensors, according to some embodiments of the present invention.
Figure 11:
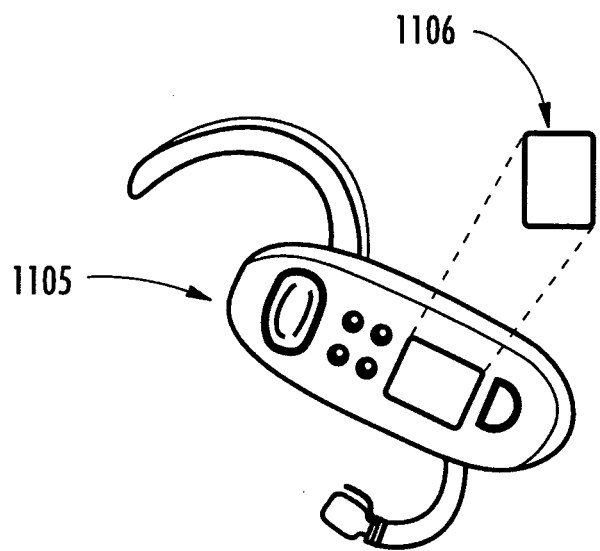
FIG. 11 is a front view of the earpiece module of FIG. 9 showing a placement of environmental sensors, according to some embodiments of the present invention.

Body temperature, including core and skin temperature, can be monitored in real-time by integrating compact infrared sensors into an earpiece module, according to some embodiments of the present invention. Infrared sensors are generally composed of thermoelectric/pyroelectric materials or semiconductor devices, such as photodiodes or photoresistors. Thermistors, thermocouples, and other temperature-dependent transducers can also be incorporated for monitoring body temperature. These sensors can be very compact and thus can be integrated throughout an earpiece module. In some embodiments, these sensors may be mounted along the backside of an earpiece body, as illustrated in FIG. 9, where the earpiece connects with the ear canal. FIG. 10 shows an embodiment of a compact sensor 1009, such as a temperature sensor, incorporated into an earpiece fitting 1008 at the backside 906 of an earpiece body 902. Because the earpiece fitting 1008 is in intimate or near-intimate contact with the ear canal, body temperature can be very accurately monitored. Signal extraction technique 600, described above, may be utilized for monitoring core body temperature via the tympanic membrane.

In some embodiments of the present invention, a pedometer can be integrated into an earpiece module to measure the number of steps walked during a day. Pedometers that can be integrated into an earpiece module include, but are not limited to, mechanical pedometers (usually implementing a metallic ball or spring), microelectromechanical systems (MEMS) pedometers, inertial sensor pedometers, accelerometer-based pedometers, accelerometry, gyroscopic pedometers, and the like.

In some embodiments of the present invention, a pedometer for an earpiece module employs an acoustic sensor for monitoring the characteristic sounds of footsteps channeled along the ear canal. For example, an acoustic sensor can be integrated into an earpiece housing (e.g., 902, FIG. 9) along the backside thereof (e.g., 906, FIG. 9) and/or within an earpiece fitting thereof (e.g., 1008, FIG. 10). The sounds generated from footsteps can be detected and analyzed with a signal processor (e.g., 405, FIG. 4) using the approach described above (i.e., 500, FIG. 5) to identify footstep sounds in the midst of convoluting physiological noise. In this embodiment, digitized electrical signals from footstep sounds from outside the body are compared with digitized electrical signals from footstep sounds traveling through the body (and ear canal), and only the spectral features associated with both types of digitized signals are amplified. This provides a new signal that contains cleaner information about footsteps. Better accuracy at discriminating a true step from other sounds or motions, such as driving in a car, can be determined by analyzing more than one sensor output through the methodology 400 described in FIG. 4.

Breathing characteristics can be monitored in a manner similar to that of acoustic pedometry (described above) in the auscultatory extraction methodology 500. In some embodiments, an acoustic sensor in an earpiece module is used to sense sounds associated with breathing. Signal processing algorithms are then used to extract breathing sounds from other sounds and noise. This information is processed into a breathing monitor, capable of monitoring, for example, the intensity, volume, and speed of breathing. Another method of monitoring breathing is to employ pressure transducers into an earpiece module. Changes in pressure inside or near the ear associated with breathing can be measured directly and, through signal processing, translated into a breathing monitor. Similarly, optical reflection sensors can be used to monitor pressure in or near the ear by monitoring physical changes in the skin or tissues in response to breathing. For monitoring the physical changes of the tympanic membrane in response to breathing, and hence ascertaining breathing rate, the optical signal extraction approach 600 described above can be employed. At least one color sensor, or colormetric sensor, can be employed to monitor changes in color associated with breathing and other health factors. In the various embodiments described herein, the location of these acoustic sensors is in or near an earpiece fitting (e.g., 1008, FIG. 10) and the sensor itself is preferably positioned in a manner similar to the sensor 1009 shown in FIG. 10.

It should be noted that some embodiments of the present invention incorporate health sensors that do not employ chemical or biological reagents for monitoring various health factors. This is because such sensors have traditionally required larger instrumentation (not suitable for portability) and/or disposable samplers (not acceptable to most end users). However, sensors employing chemical or biological reagents may be incorporated into earpiece modules, according to some embodiments of the present invention. For example, the diffusion of analyte through the skin can be monitored electrically or optically by selective binding to enzymes or antibodies contained in the health sensors integrated into an earpiece module. In some cases, iontophoresis, agitation, heat, or osmosis may be required to pull ions from the skin or blood into the sensor region for monitoring health factors. In some cases, these analytes may be tagged with markers for electromagnetic, electrical, nuclear, or magnetic detection.

Caloric intake, physical activity, and metabolism can be monitored using a core temperature sensor, an accelerometer, a sound extraction methodology (e.g., 500, FIG. 5) a pulse oximeter, a hydration sensor, and the like. These sensors can be used individually or in unison to assess overall caloric metabolism and physical activity for purposes such as diet monitoring, exercise monitoring, athletic training, or the like. For example, the sound extraction methodology 500 of FIG. 5 can be used to extract sounds associated with swallowing, and this can give an indication of total food volume consumed. Additionally, a core temperature sensor, such as a thermopile, a pyroelectric sensor, a thermoelectric sensor, or a thermistor, or a tympanic membrane extraction technique (e.g., 600, FIG. 6), can be used to assess metabolism. In one case, the core temperature is compared with the outdoor temperature, and an estimate of the heat loss from the body is made, which is related to metabolism.

Environmental temperature can be monitored, for example, by thermistor, thermocouple, diode junction drop reference, or the like. Electrical temperature measurement techniques are well known to those skilled in the art, and are of suitable size and power consumption that they can be integrated into a wireless earpiece module without significant impact on the size or functionality of the wireless earpiece module.

Environmental noise can be monitored, for example, by a transducer, microphone, or the like. Monitoring of environmental noise preferably includes, but is not limited to, instantaneous intensity, spectral frequency, repetition frequency, peak intensity, commonly in units of decibels, and cumulative noise level exposures, commonly in units of decibel-hours. This environmental noise may or may not include noise generated by a person wearing an earpiece module. Sound made by a person wearing an earpiece module may be filtered out, for example, using analog or digital noise cancellation techniques, by directional microphone head shaping, or the like. The environmental noise sensor may or may not be the same sensor as that used for the intended purpose of wireless communication. In some embodiments, the environmental noise sensor is a separate sensor having broader audible detection range of noise level and frequency, at the possible sacrifice of audio quality.

Environmental smog includes VOC's, formaldehyde, alkenes, nitric oxide, PAH's, sulfur dioxide, carbon monoxide, olefins, aromatic compounds, xylene compounds, and the like. Monitoring of the aforementioned smog components can be performed using earpiece modules and other wearable apparatus, according to embodiments of the present invention, in a variety of methods. All smog components may be monitored. Alternatively, single smog components or combinations of smog components may be monitored. Photoionization detectors (PID's) may be used to provide continuous monitoring and instantaneous readings. Other methods of detecting smog components according to embodiments of the present invention include, but are not limited to, electrocatalytic, photocatalytic, photoelectrocatalytic, calorimetric, spectroscopic or chemical reaction methods. Examples of monitoring techniques using the aforementioned methods may include, but are not limited to, IR laser absorption spectroscopy, difference frequency generation laser spectroscopy, porous silicon optical microcavities, surface plasmon resonance, absorptive polymers, absorptive dielectrics, and calorimetric sensors. For example, absorptive polymer capacitors inductors, or other absorptive polymer-based electronics can be incorporated into an earpiece module (e.g., 100, FIG. 1) according to embodiments of the present invention. These polymers change size or electrical or optical properties in response to analyte(s) from the environment (such as those described above). The electrical signal from these absorptive polymer electronic sensors can be correlated with the type and intensity of environmental analyte. Other techniques or combinations of techniques may also be employed to monitor smog components. For example, a smog component may be monitored in addition to a reference, such as oxygen, nitrogen, hydrogen, or the like. Simultaneous monitoring of smog components with a reference analyte of known concentration allows for calibration of the estimated concentration of the smog component with respect to the reference analyte within the vicinity of an earpiece user.

In some embodiments of the present invention, environmental air particles can be monitored with a flow cell and a particle counter, particle sizer, particle identifier, or other particulate matter sensor incorporated as part of an earpiece module (e.g., 100, FIG. 1) or externally attached to an earpiece module. Non-limiting examples of particles include oil, metal shavings, dust, smoke, ash, mold, or other biological contaminates such as pollen. In some embodiments of the present invention, a sensor for monitoring particle size and concentration is an optical particle counter. A light source is used (e.g., a laser or a laser diode), to illuminate a stream of air flow. However, a directional LED beam, generated by a resonant cavity LED (RCLED), a specially lensed LED, or an intense LED point source, can also be used for particle detection. The optical detector which is off-axis from the light beam measures the amount of light scattered from a single particle by refraction and diffraction. Both the size and the number of particles can be measured at the same time. The size of the monitored particle is estimated by the intensity of the scattered light. Additionally, particles can be detected by ionization detection, as with a commercial ionization smoke detector. In this case, a low-level nuclear radiation source, such as americium-241, may be used to ionize particles in the air between two electrodes, and the total ionized charge is detected between the electrodes. As a further example, piezoelectric crystals and piezoelectric resonator devices can be used to monitor particles in that particles reaching the piezoelectric surface change the mass and hence frequency of electromechanical resonance, and this can be correlated with particle mass. If the resonators are coated with selective coatings, certain types of particles can attach preferentially to the resonator, facilitating the identification of certain types of particles in the air near a person wearing an earpiece module. In some embodiments, these resonators are solid state electrical devices, such as MEMS devices, thin film bulk acoustic resonators (FBARs), surface-acoustic wave (SAW) devices, or the like. These compact solid state components may be arrayed, each arrayed element having a different selective coating, for monitoring various types of particles.

In some embodiments of the present invention, environmental air pressure or barometric pressure can be monitored by a barometer. Non-limiting examples of barometric pressure measurement include hydrostatic columns using mercury, water, or the like, foil-based or semiconductor-based strain gauge, pressure transducers, or the like. In some embodiments of the present invention, semiconductor-based strain gauges are utilized. A strain gauge may utilize a piezoresistive material that gives an electrical response that is indicative of the amount of deflection or strain due to atmospheric pressure. Atmospheric pressure shows a diurnal cycle caused by global atmospheric tides. Environmental atmospheric pressure is of interest for prediction of weather and climate changes. Environmental pressure may also be used in conjunction with other sensing elements, such as temperature and humidity to calculate other environmental factors, such as dew point. Air pressure can also be measured by a compact MEMS device composed of a microscale diaphragm, where the diaphragm is displaced under differential pressure and this strain is monitored by the piezoelectric or piezoresistive effect.

In some embodiments of the present invention, environmental humidity, relative humidity, and dew point can be monitored by measuring capacitance, resistivity or thermal conductivity of materials exposed to the air, or by spectroscopy changes in the air itself. Resistive humidity sensors measure the change in electrical impedance of a hygroscopic medium such as a conductive polymer, salt, or treated substrate. Capacitive humidity sensors utilize incremental change in the dielectric constant of a dielectric, which is nearly directly proportional to the relative humidity of the surrounding environment. Thermal humidity sensors measure the absolute humidity by quantifying the difference between the thermal conductivity of dry air and that of air containing water vapor. Humidity data can be stored along with pressure monitor data, and a simple algorithm can be used to extrapolate the dew point. In some embodiments of the present invention, monitoring humidity is performed via spectroscopy. The absorption of light by water molecules in air is well known to those skilled in the art. The amount of absorption at known wavelengths is indicative of the humidity or relative humidity. Humidity may be monitored with a spectroscopic method that is compatible with the smog monitoring spectroscopic method described above.

When environmental factors such as the aforementioned are monitored continuously in real-time, a user's total exposure level to an environmental factor can be recorded. When a representative volume of air a user has been exposed to is monitored or estimated, the volumetric concentration of the analytes can be calculated or estimated. In order to estimate the volume of air a person wearing the earpiece has been exposed to, a pedometer or accelerometer or air flow sensor can also be integrated into an earpiece module. Pedometers and accelerometers can be integrated into an earpiece module via mechanical sensors (usually implementing a mechanical-electrical switch), MEMS devices, and/or gyroscopic technologies. The technologies required for these types of pedometers and accelerators are well known to those skilled in the art. The incorporated pedometer or accelerometer (or more than one pedometer or accelerometer) is used to gage the distance a person has traveled, for use in the estimation of the volume of air to which a person has been exposed, and the subsequent estimate of the volumetric concentration of monitored analytes.

The health and environmental sensors utilized with earpiece modules and other wearable monitoring apparatus, according to embodiments of the present invention, can operate through a user-selectable switch on an earpiece module. However, health and environmental sensors can also be run automatically and independently of the person wearing the apparatus. In other embodiments, the person may control health and environmental monitoring through a device wirelessly coupled to an earpiece module, such as a portable telecommunication device (e.g., 210, FIG. 2). For example, health and environmental sensors in or about an earpiece module can be controlled wirelessly through, for example, a cell phone, laptop, or personal digital assistant (PDA).

The earpiece module 100 may be configured such that user preferences can be "downloaded" wirelessly without requiring changes to the earpiece monitor hardware. For example, an earpiece concerned about a heart condition may wish to have the signal processor 103 focus on processing pulse signature, at the expense of ignoring other physiological or environmental parameters. The user may then use the portable telecommunication device 210 to download a specialized algorithm through the web. This may be accomplished through existing wireless infrastructure by text-messaging to a database containing the algorithm. The user will then have an earpiece module suited with analysis software specialized to the needs and desires of the user.

Health and environmental monitors, according to embodiments of the present invention, enable low-cost, real-time personal health and environmental exposure assessment monitoring of various health factors. An individual's health and environmental exposure record can be provided throughout the day, week, month, or the like. Moreover, because the health and environmental sensors can be small and compact, the overall size of an apparatus, such as an earpiece, can remain lightweight and compact.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An earpiece module, comprising:
   an earpiece fitting adapted to be positioned within an ear of a person, the earpiece fitting comprising:
      a speaker configured to provide sound transmission from a source;
      an optical emitter, optical detector, and acoustic sensor, wherein the optical emitter is configured to direct optical energy to a region of the ear of the person, wherein the optical detector is configured to sense secondary optical energy emanating from the ear region and to sense at least one environmental condition in a vicinity of the person, and wherein the acoustic sensor is configured to sense footsteps of the person; and
      a first signal processor configured to receive and process signals produced by the optical detector;
   a second signal processor configured to process signals produced by the first signal processor, and by the acoustic sensor, and to selectively remove unwanted environmental signals and unwanted signals from footsteps to produce processed signals containing cleaner physiological information from the person; and
   a transmitter responsive to the second signal processor that is configured to transmit the processed signals containing cleaner physiological information to a remote terminal.

2. The earpiece module of claim 1, wherein the transmitter is configured to transmit the signals containing cleaner physiological information from the second signal processor to the remote terminal in real time.

3. The earpiece module of claim 1, wherein the first signal processor is configured to process signals produced by the optical detector into signals that can be heard and/or viewed by the person.

4. The earpiece module of claim 1, wherein the optical detector is configured to detect blackbody IR radiation emanating from the tympanic membrane of the ear of the person.

5. The earpiece module of claim 1, wherein the ear region is the tympanic membrane, wherein the optical emitter directs optical energy towards the tympanic membrane, and wherein optical detector senses secondary optical energy emanating from the tympanic membrane.

6. The earpiece module of claim 5, wherein the first signal processor is configured to extract selected optical energy from the secondary optical energy emanating from the tympanic membrane.

7. The earpiece module of claim 5, wherein the first signal processor is configured to extract or remove optical noise from the secondary optical energy emanating from the tympanic membrane.

8. The earpiece module of claim 1, wherein the optical detector comprises an optical filter configured to pass secondary optical energy at selective wavelengths.

9. The earpiece module of claim 1, wherein the first signal processor utilizes one or more filters to process signals produced by the optical detector.

10. The earpiece module of claim 1, further comprising a receiver configured to receive audio information from the remote terminal, and further comprising a communication module that is configured to store and/or process and/or play audio information received from the remote terminal via the speaker.

11. The earpiece module of claim 1, further comprising a communication module that is configured to alert the person when the optical detector senses certain physiological information from the person and/or certain environmental information from the vicinity of the person.

12. The earpiece module of claim 11, wherein the communication module is configured to provide audible and/or visible alerts and/or physical alerts.

13. The earpiece module of claim 11, wherein the communication module is configured to audibly present vital sign information to the person.

14. The earpiece module of claim 11, wherein the communication module is configured to store content generated by the person and/or by the optical detector.

15. The earpiece module of claim 1, wherein the transmitter is configured to transmit signals produced by the optical detector to a gaming device.

16. The earpiece module of claim 1, further comprising a transmittance pulse oximeter and/or reflectance pulse oximeter.

17. The earpiece module of claim 1, further comprising one or more sonic and pressure transducers that are configured to measure blood pressure of the person.

18. The earpiece module of claim 1, further comprising electrodes configured to monitor electrical signals from the person.

19. The earpiece module of claim 1, further comprising a motion sensor configured to sense body motion of the person.

20. The earpiece module of claim 19, wherein the motion sensor comprises an accelerometer and/or gyroscope.

21. The earpiece module of claim 1, further comprising a body temperature sensor.

22. The earpiece module of claim 1, wherein the earpiece fitting further comprises a colorimetric sensor that changes color in response to sensing one or more chemicals in the environment.

23. The earpiece module of claim 1, wherein the earpiece fitting further comprises a pedometer.

24. The earpiece module of claim 1, wherein the earpiece fitting further comprises an acoustical sensor that senses sound generated by footsteps.

25. The earpiece module of claim 1, wherein the earpiece fitting further comprises an acoustical sensor that senses breathing.

26. The earpiece module of claim 1, wherein the earpiece fitting further comprises an electromagnetic field (EMF) sensor that is configured to sense electromagnetic radiation spikes.

27. The earpiece module of claim 1, wherein the earpiece fitting further comprising an air sampling system that samples air in a vicinity of the person.

28. The earpiece module of claim 1, wherein the earpiece fitting further comprises an ozone sensor or a carbon monoxide sensor.

29. The earpiece module of claim 1, wherein the optical detector comprises an ultraviolet (UV) light sensor.

30. The earpiece module of claim 1, further comprising a recording device that records signals produced by the optical detector and/or signals processed by the first or second signal processors.

31. The earpiece module of claim 1, further comprising a user interface that provides user control over the optical detector, the acoustic sensor, the first signal processor, or the second signal processor.

32. The earpiece module of claim 1, further comprising a user interface that is configured to allow the person to store a time mark indicating a particular point in time.

33. The earpiece module of claim 1, wherein the transmitter is configured to send a signal to the remote terminal when the optical detector is turned off.

34. The earpiece module of claim 1, wherein the transmitter is configured to send a signal to the remote terminal when potentially erroneous data has been collected by the optical detector.

35. The earpiece module of claim 1, wherein the optical detector is configured to sense information associated with damage to a portion of the body of the person.

36. The earpiece module of claim 35, further comprising a communication module that is configured to alert the person when the optical detector senses information associated with damage to a portion of the body of the person.

37. The earpiece module of claim 1, wherein the optical detector is configured to monitor one or more of the following types of physiological information: heart rate, pulse rate, breathing rate, blood flow, heartbeat signatures, cardio-pulmonary health, organ health, metabolism, electrolyte type and/or concentration, physical activity, caloric intake, caloric metabolism, physical and/or psychological stress levels and/or stress level indicators, drug dosage and/or dosimetry, physiological drug reactions, drug chemistry, biochemistry, position and/or balance, body strain, neurological functioning, brain activity, brain waves, blood pressure, cranial pressure, hydration level, auscultatory information, auscultatory signals associated with pregnancy, physiological response to infection, skin and/or core body temperature, eye muscle movement, blood volume, inhaled and/or exhaled breath volume, physical exertion, exhaled breath physical and/or chemical composition, the presence and/or identity and/or concentration of viruses and/or bacteria, foreign matter in the body, internal toxins, heavy metals in the body, anxiety, fertility, ovulation, sex hormones, psychological mood, sleep patterns, hunger and/or thirst, hormone type and/or concentration, cholesterol, lipids, blood panel, bone density, organ and/or body weight, reflex response, sexual arousal, mental and/or physical alertness, sleepiness, auscultatory information, response to external stimuli, swallowing volume, swallowing rate, sickness, voice characteristics, voice tone, voice pitch, voice volume, vital signs, head tilt, allergic reactions, inflammation response, auto-immune response, mutagenic response, DNA, proteins, protein levels in the blood, water content of the blood, pheromones, internal body sounds, digestive system functioning, cellular regeneration response, healing response, stem cell regeneration response.

38. The earpiece module of claim 1, wherein the optical detector is configured to monitor one or more of the following types of environmental information: climate, humidity, temperature, pressure, barometric pressure, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, optical radiation, X-rays, gamma rays, microwave radiation, terahertz radiation, ultraviolet radiation, infrared radiation, radio waves, atomic energy alpha particles, atomic energy beta-particles, gravity, light intensity, light frequency, light flicker, light phase, ozone, carbon monoxide, carbon dioxide, nitrous oxide, sulfides, airborne pollution, foreign material in the air, viruses, bacteria, signatures from chemical weapons, wind, air turbulence, sound and/or acoustical energy, ultrasonic energy, noise pollution, human voices, animal sounds, diseases expelled from others, exhaled breath and/or breath constituents of others, toxins from others, pheromones from others, industrial and/or transportation sounds, allergens, animal hair, pollen, exhaust from engines, vapors and/or fumes, fuel, signatures for mineral deposits and/or oil deposits, snow, rain, thermal energy, hot surfaces, hot gases, solar energy, hail, ice, vibrations, traffic, the number of people in a vicinity of the person, coughing and/or sneezing sounds from people in the vicinity of the person, loudness and/or pitch from those speaking in the vicinity of the person.

39. The earpiece module of claim 1, further comprising a microphone and transceiver, wherein the transceiver is electronically connected to the speaker and microphone and permits bidirectional wireless communications between the earpiece module and the remote terminal, and wherein the transceiver is electronically connected to the second signal processor and is configured to transmit physiological and environmental signals from the second signal processor to the remote terminal.

40. The earpiece module of claim 39, wherein the transceiver is a short-range wireless transmission, Wi-Fi, or ZigBee transceiver or is interoperable with multiple wireless communication protocols.

41. The earpiece module of claim 1, wherein the transmitter is configured to transmit signals from the second signal processor to the remote terminal following a predetermined time interval.

42. The earpiece module of claim 1, wherein the first or second signal processor is configured to identify a person to whom the personal monitoring apparatus housing is attached.

43. The earpiece module of claim 1, wherein the first or second signal processor is configured to monitor physical aging rate.

44. The earpiece module of claim 1, wherein the first or second signal processor is configured to processes information from the optical detector to assess aging rate.

45. The earpiece module of claim 1, wherein the earpiece fitting further comprises a UV sensor or a pollution sensor.

46. The earpiece module of claim 1, wherein the earpiece fitting further comprises a pulse rate sensor, a blood pressure sensor, an activity sensor, or a psychosocial stress sensor.

47. The earpiece module of claim 1, wherein the earpiece fitting is a hearing aid.

48. The earpiece module of claim 1, further comprising memory that includes at least one algorithm, and wherein the first or second signal processor is configured to process the at least one algorithm.

49. The earpiece module of claim 48, wherein the at least one algorithm can be modified wirelessly via the transmitter.

50. The earpiece module of claim 48, wherein the transmitter is configured to wirelessly upload an algorithm to the memory.

51. The earpiece module of claim 48, wherein the at least one algorithm is configured to focus processing resources on at least one extraction of physiological or environmental information.

52. The earpiece module of claim 1, further comprising a rechargeable power source that powers the optical emitter, optical detector, acoustic sensor, the first and second signal processors, and the transmitter.

53. The earpiece module of claim 11, wherein the communication module communicates a treatment, therapy, or plan of action to the person in response to physiological or environmental concerns.

54. The earpiece module of claim 1, further comprising an audible communicator that is configured to communicate therapeutic sounds to the person via the speaker in response to physiological or psychosocial stress.

55. The earpiece module of claim 1, wherein the earpiece fitting further comprises a light source that is configured to provide light therapy to the person in response to physiological or psychosocial stress.

56. The earpiece module of claim 1, wherein the earpiece fitting further comprises multiple temperature sensors configured to measure core body temperature and skin temperature of the person.

57. The earpiece module of claim 55, wherein the temperature sensors are configured to measure core body temperature from the tympanic membrane or ear canal and skin temperature from the skin of the ear canal or the skin of the outer ear.

* * * * *